(12) United States Patent
Wang et al.

(10) Patent No.: US 10,011,614 B2
(45) Date of Patent: Jul. 3, 2018

(54) BIS-β-CARBOLINE COMPOUND AND PREPARATION METHOD, PHARMACEUTICAL COMPOSITION AND USE THEREOF

(71) Applicant: XINJIANG HUASHIDAN PHARMACEUTICAL RESEARCH CO., LTD., Urumqi (CN)

(72) Inventors: Zihou Wang, Urumqi (CN); Jialin Wu, Urumqi (CN); Jing Shang, Urumqi (CN); Qin Ma, Urumqi (CN); Buxi Shi, Urumqi (CN); Liang Guo, Urumqi (CN); Wenxi Fan, Urumqi (CN); Jie Sun, Urumqi (CN)

(73) Assignee: Xinjiang Huashidan Pharmaceutical Research Co., Ltd, Xinjiang (CN)

( * ) Notice: Subject to any disclaimer, the term of this patent is extended or adjusted under 35 U.S.C. 154(b) by 61 days.

(21) Appl. No.: 14/647,318

(22) PCT Filed: Nov. 26, 2012

(86) PCT No.: PCT/CN2012/085296
§ 371 (c)(1),
(2) Date: Oct. 19, 2015

(87) PCT Pub. No.: WO2014/079070
PCT Pub. Date: May 30, 2014

(65) Prior Publication Data
US 2016/0039845 A1 Feb. 11, 2016

(51) Int. Cl.
*C07D 519/00* (2006.01)
*C07D 471/04* (2006.01)

(52) U.S. Cl.
CPC ......... *C07D 519/00* (2013.01); *C07D 471/04* (2013.01)

(58) Field of Classification Search
CPC .............................. C07D 519/00; C07D 471/04
USPC ........................................................ 546/79
See application file for complete search history.

(56) References Cited

U.S. PATENT DOCUMENTS 2,048,622 A 7/1936 Pyman et al.

FOREIGN PATENT DOCUMENTS

| CN | 101429198 A | 5/2009 |
| CN | 102796124 A | 11/2012 |
| WO | 2009047298 A | 4/2009 |

OTHER PUBLICATIONS

Caplus English abstract Allan Gray, 1954, Bisammonium salts. Derivatives of some carboline and related heterocyclic bases.*
Rook et al., "Bivalent ß-Carbolines as Potential Multi-Target Anti-Alzheimer Agents", Journal of Medicinal Chemistry, Apr. 5, 2010, vol. 53, No. 9, p. 3613.
Gray et al., "Bis ammonium salts, Derivatives of some carboline and related heterocyclic bases", Journal of the American Chemical Society, May 20, 1954, vol. 76, p. 2796.
Song et al., "ß-Carbolines as specific inhibitors of cyclin-dependent kinases", Bioorganic & Medicinal Chemistry Letters, (2002) vol. 12, No. 7, p. 1131.
Agarwal et al. "Synthesis of neoeudistomin analogs as potential filaricides", Bioorganic & Medicinal Chemistry Letters (1995) vol. 5 No. 14, p. 1546.
Mokrosz et al., Structure-activity relationship studies of CNS agents. Part 1: the Free-Wilson analysis of acute toxicity and sedative effect of some 1,2,3,4-tetrahydro-ß-carbolines, Pharmazie (1990) vol. 45, No. 10, p. 765.
International Search Report dated Sep. 15, 2013.

* cited by examiner

*Primary Examiner* — Rita J Desai
(74) *Attorney, Agent, or Firm* — Dilworth & Barrese, LLP

(57) ABSTRACT

Disclosed in the present invention are a bis-β-carboline compound and a preparation method, a pharmaceutical composition and the use thereof. In particular, the bis-β-carboline compound and a pharmaceutical salt thereof are described as general formula I, and the bis-β-carboline compound is prepared through the condensation of β-carboline intermediate and dihaloalkane. Also disclosed in the present invention are a pharmaceutical composition comprising an effective dose of the bis-β-carboline compound as shown in formula I and a pharmaceutically acceptable carrier, and the use of the bis-β-carboline compound in preparing drugs resistant to tumors such as melanoma, stomach cancer, lung cancer, breast cancer, kidney cancer, liver cancer, oral epidermoid carcinoma, cervical cancer, ovarian cancer, pancreatic cancer, prostate cancer, and colon cancer.

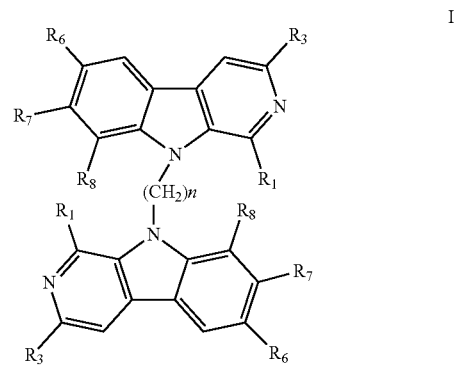

3 Claims, No Drawings

BIS-β-CARBOLINE COMPOUND AND PREPARATION METHOD, PHARMACEUTICAL COMPOSITION AND USE THEREOF

FIELD OF THE INVENTION

The present invention relates to a class of bis-β-carboline alkaloid compounds and pharmaceutically acceptable salts, their preparation, as well as pharmaceutical compositions comprising such compounds, and its application in the preparation of anti-tumor drugs; belongs to the technical field of medicine.

BACKGROUND OF THE INVENTION

Cook et al. (2005, 2010) reported the synthesis method of bis-β-carboline of 6-alkynyl bridge connection, subsequently confirmed that such bis-β-carboline alkaloids has a good affinity on benzodiazepine receptor (Bz) and γ-aminobutyric acid (GABA) receptor.

Winckler et al. (2010) designed the bis-3,4-dihydro-β-carboline and bis-β-carboline compounds of two methylene bridge connecting and 9-methylene bridge connecting, and demonstrated that these compounds have better inhibitory activity on acetylcholinesterase and butyrylcholinesterase Zheng et al. synthesized bis-3,4-dihydro-β-carboline and bis-β-carboline compound of the 9-methylene bridge connecting and 11C-labeled according to the synthesis methods of Winckler et al, and found that such bis-β-carboline compounds can be used as a new imaging agent of the positive radiation tomography for acetylcholinesterase imaging in Alzheimer's disease (AD) patient, but the role of these compounds in anti-tumor were not disclosed.

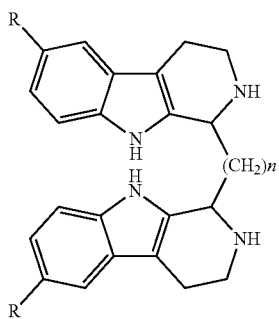

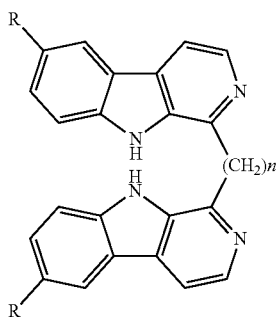

R = H, OCH₃
n = 4, 6, 8, 10

The bis-β-carboline reported in the literature was bridge connected in the 1 position.

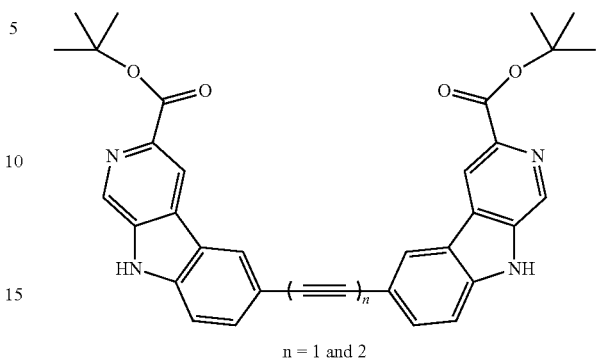

n = 1 and 2

The bis-β-carboline reported in the literature was bridge connected in the 6 position.

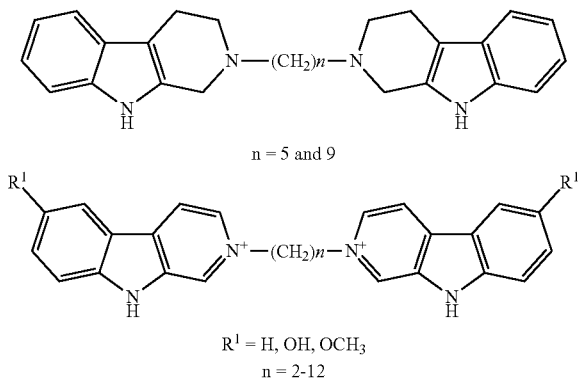

n = 5 and 9

$R^1$ = H, OH, OCH₃
n = 2-12

The bis-β-carboline reported in the literature was bridge connected in the 2 position.

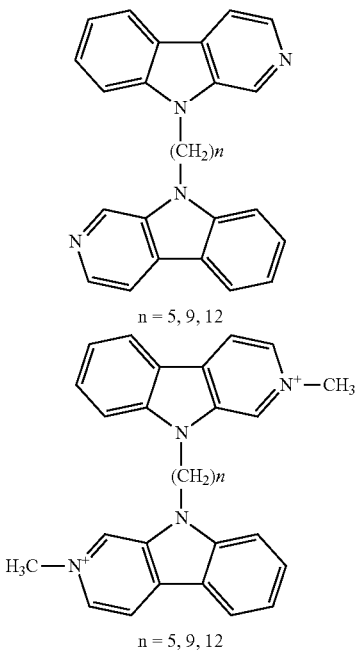

n = 5, 9, 12 n = 5, 9, 12

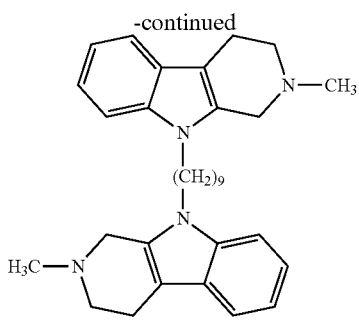

The bis-β-carboline reported in the literature was bridge connected in the 9 position.

DETAILED DESCRIPTION OF THE INVENTION

The technical problem solved by the present invention is to provide a new class of anti-tumor compound, an bis-β-carboline which was bridge connected in the 9 position.

The second technical problem solved by the present invention is to provide a process for preparation method of an bis-β-carboline compound.

The third technical problem solved by the present invention is to provide a pharmaceutical composition, comprising the bis-β-carboline compound.

The forth technical problem solved by the present invention is to provide the use of the bis-β-carboline compound in preparing drugs resistant to tumours In order to solve the above technical problems, the present invention provides the following technical solutions: an bis-β-carboline which are bridge connected in the 9 position and a pharmaceutical salt thereof are described as general formula I

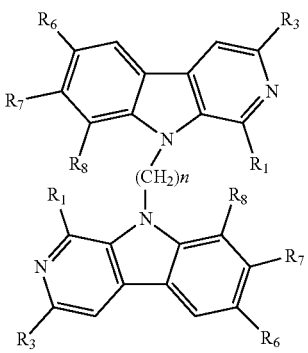

wherein,
$R_1$ is substituent selected from the group consisting of hydrogen, substituted or unsubstituted C1-6 linear or branched alkyl, hydroxyl, substituted or unsubstituted C1-6 linear or branched alkoxy, sulfonate group, substituted or unsubstituted C1-6 linear or branched alkylthio, C1-6 alkoxy C1-6 alkyl group, amino group, substituted or unsubstituted C1-6 linear or branched alkylamino group wherein the alkylamino group include mono- and bis-alkylamino, halogen, nitro, cyano, substituted or unsubstituted five-six membered aryl, substituted or unsubstituted five-six membered aryl containing 1-4 heteroatoms selected from N, O, or S;

Substituents on the substituted or unsubstituted C1-6 linear or branched alkyl are selected from the group consisting of hydroxy, mercapto, amino, aldehyde, carboxyl, carbamoyl, halogen, nitro, and cyano;

Substituents on the substituted or unsubstituted five-six membered aryl are selected from the group consisting of hydroxy, mercapto, amino, aldehyde, carboxyl, carbamoyl, halogen, nitro, cyano, C1-6 alkyl, C1-6 alkoxy, C1-6 alkylamino, C1-6 alkylamino group and C1-6 alkoxy C1-6 alkyl group;

Substituents on the substituted or unsubstituted five-six membered aryl containing 1-4 heteroatoms selected from N, O, or S; are selected from the group consisting of hydroxy, mercapto, amino, aldehyde, carboxyl, carbamoyl, halogen, nitro, cyano, C1-6 alkyl, C1-6 alkoxy, C1-6 alkylamino, C1-6 alkylamino group and C1-6 alkoxy C1-6 alkyl group;

Preferably, $R_1$ is substituent selected from the group consisting of hydrogen, substituted or unsubstituted C1-6 linear or branched alkyl, substituted or unsubstituted five-six membered aryl, substituted or unsubstituted five-six membered aryl containing 1-4 heteroatoms selected from N, O, or S;

Preferably, five-membered aryl is selected from

,

Preferably, six-membered aryl is selected from

,

Preferably, five-membered aryl containing 1-4 heteroatoms selected from N, O, or S is selected from:

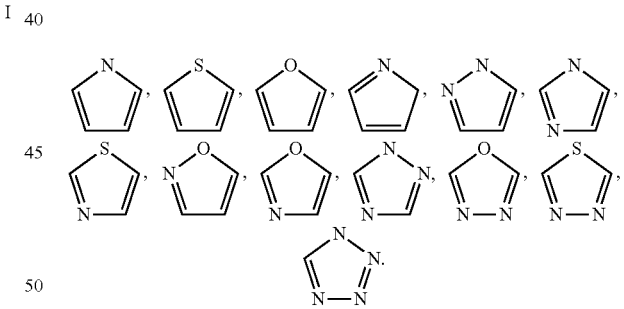

Preferably, six-membered aryl containing 1-4 heteroatoms selected from N, O, or S is selected from:

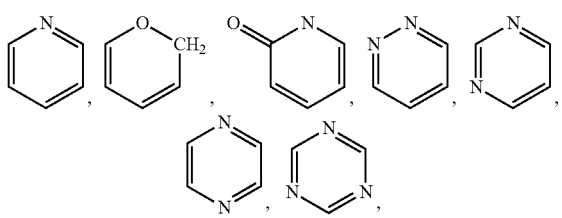

More Preferably $R_1$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, carboxyl, substituted or unsubstituted C1-4 linear or branched alkyl-ester group, substituted or unsubstituted C1-4 linear or branched alkyl acyloxy, carbamoyl, substituted or unsubstituted C1-4 linear or branched alkyl acylamino group, C2-4 olefins, halogen, nitro, cyano, substituted or unsubstituted phenyl, substituted or unsubstituted pyridine and substituted or unsubstituted thiophene;

Substituents on the substituted or unsubstituted C1-4 linear or branched alkyl are selected from the group consisting of hydroxy, mercapto, amino, aldehyde, carboxyl, carbamoyl, fluoro, chloro, bromo, nitro, and cyano;

Substituents on the substituted or unsubstituted phenyl are selected from the group consisting of hydroxy, mercapto, amino, aldehyde, carboxyl, carbamoyl, fluoro, chloro, bromo, nitro, cyano, C1-4alkyl, C1-4 alkoxy, C1-4 alkylamino, and C1-4 alkoxy C1-4 alkyl group;

Substituents on the substituted or unsubstituted pyridine are selected from the group consisting of hydroxy, mercapto, amino, aldehyde, carboxyl, carbamoyl, fluoro, chloro, brom, nitro, cyano, C1-4alkyl, C1-4 alkoxy, C1-4 alkylamino, and C1-4 alkoxy C1-4 alkyl group;

Substituents on the substituted or unsubstituted thiophene are selected from the group consisting of hydroxy, mercapto, amino, aldehyde, carboxyl, carbamoyl, fluoro, chloro, bromo, nitro, cyano, C1-4alkyl, C1-4 alkoxy, C1-4 alkylamino, and C1-4 alkoxy C1-4 alkyl group;

Most preferably $R_1$ is substituent selected from the group consisting of hydrogen, methyl, ethyl, propyl, isopropyl, butyl, phenyl, pyridine and thiophene.

$R_3$ is substituent selected from the group consisting of hydrogen, substituted or unsubstituted C1-6 linear or branched alkyl carconby, carboxyl; substituted or unsubstituted C1-6 linear or branched alkoxy carconby, substituted or unsubstituted C1-6 linear or branched alkyl carbonyloxy, amino-carbonyl, substituted or unsubstituted C1-6 linear or branched alkylamino carbonyloxy, substituted or unsubstituted C1-6 linear or branched alkyl acyl amido More preferably $R_3$ is substituent selected from the group consisting of hydrogen, C1-6 alkoxy-CO—, C1-4alkyl-NH—CO—;

Most preferably $R_3$ is substituent selected from the group consisting of hydrogen, methoxy, ethoxy, propoxy, isopropoxy, butoxy, pentyloxy, isopentyloxy, methyl-NH—CO—, ethyl-NH—CO—, propyl-NH—CO—, isopropyl-NH—CO—, butyl-NH—CO—, pentyloxy-NH—CO—, isopentyloxy-NH—CO—;

$R_6$ is substituent selected from the group consisting of hydrogen, substituted or unsubstituted C1-6 linear or branched alkyl, hydroxyl, substituted or unsubstituted C1-6 linear or branched alkoxy, sulfonate group, substituted or unsubstituted C1-6 linear or branched alkylthio, C1-6 alkoxy C1-6 alkyl group, amino group, substituted or unsubstituted C1-6 linear or branched alkylamino group wherein the alkylamino group include mono- and bis-alkylamino, aldehyde, substituted or unsubstituted C1-6 linear or branched alkyl acyl, substituted or unsubstituted C1-6 linear or branched alkyloxy acyl, carboxyl, substituted or unsubstituted C1-6 linear or branched alkyl acyloxy, carbamoyl, substituted or unsubstituted C1-6 linear or branched alkyl acylamino group, substituted or unsubstituted C1-6 linear or branched alkyl acylamino group, C2-6 olefins, halogen, nitro, cyano;

More preferably $R_6$ is substituent selected from the group consisting of hydrogen, nitro, halogen, substituted or unsubstituted C1-6 linear or branched alkyl, hydroxyl, substituted or unsubstituted C1-6 linear or branched alkoxy, mercapto, amino, aldehyde, carboxyl, cyano;

Most preferably $R_6$ is substituent selected from the group consisting of hydrogen, nitro, fluoro, chloro, bromo, methyl, ethyl, propyl, isopropyl, butyl, pentyl, isopentyl, hydroxyl, methoxy, ethoxy, propoxy, isopropoxy, butoxy, pentyloxy, isopentyloxy, hydroxy, mercapto, amino, aldehyde, carboxyl, cyano;

$R_7$ is substituent selected from the group consisting of hydrogen, substituted or unsubstituted C1-6 linear or branched alkyl, hydroxyl, substituted or unsubstituted C1-6 linear or branched alkoxy, sulfonate group, substituted or unsubstituted C1-6 linear or branched alkylthio, C1-6 alkoxy C1-6 alkyl group, amino group, substituted or unsubstituted C1-6 linear or branched alkylamino group wherein the alkylamino group include mono- and bis-alkylamino, aldehyde, substituted or unsubstituted C1-6 linear or branched alkyl acyl, substituted or unsubstituted C1-6 linear or branched alkyloxy acyl, carboxyl, substituted or unsubstituted C1-6 linear or branched alkyl acyloxy, carbamoyl, substituted or unsubstituted C1-6 linear or branched alkyl acylamino group, substituted or unsubstituted C1-6 linear or branched alkyl acylamino group, C2-6 olefins, halogen, nitro, cyano;

More preferably $R_7$ is substituent selected from the group consisting of hydrogen, nitro, halogen, substituted or unsubstituted C1-6 linear or branched alkyl, hydroxyl, substituted or unsubstituted C1-6 linear or branched alkoxy, mercapto, amino, aldehyde, carboxyl, cyano;

Most preferably $R_7$ is substituent selected from the group consisting of hydrogen, nitro, fluoro, chloro, bromo, methyl, ethyl, propyl, isopropyl, butyl, pentyl, isopentyl, hydroxyl, methoxy, ethoxy, propoxy, isopropoxy, butoxy, pentyloxy, isopentyloxy, hydroxy, mercapto, amino, aldehyde, carboxyl, cyano;

$R_8$ is substituent selected from the group consisting of hydrogen, substituted or unsubstituted C1-6 linear or branched alkyl, hydroxyl, substituted or unsubstituted C1-6 linear or branched alkoxy, sulfonate group, substituted or unsubstituted C1-6 linear or branched alkylthio, C1-6 alkoxy C1-6 alkyl group, amino group, substituted or unsubstituted C1-6 linear or branched alkylamino group wherein the alkylamino group include mono- and bis-alkylamino, aldehyde, substituted or unsubstituted C1-6 linear or branched alkyl acyl, substituted or unsubstituted C1-6 linear or branched alkyloxy acyl, carboxyl, substituted or unsubstituted C1-6 linear or branched alkyl acyloxy, carbamoyl, substituted or unsubstituted C1-6 linear or branched alkyl acylamino group, substituted or unsubstituted C1-6 linear or branched alkyl acylamino group, C2-6 olefins, halogen, nitro, cyano;

More preferably $R_8$ is substituent selected from the group consisting of hydrogen, nitro, halogen, substituted or unsubstituted C1-6 linear or branched alkyl, hydroxyl, substituted or unsubstituted C1-6 linear or branched alkoxy, mercapto, amino, aldehyde, carboxyl, cyano;

Most preferably $R_8$ is substituent selected from the group consisting of hydrogen, nitro, fluoro, chloro, bromo, methyl, ethyl, propyl, isopropyl, butyl, pentyl, isopentyl, hydroxyl, methoxy, ethoxy, propoxy, isopropoxy, butoxy, pentyloxy, isopentyloxy, hydroxy, mercapto, amino, aldehyde, carboxyl, cyano;

n is selected from the group consisting of the natural numbers from 2 to 12. In other words, n is selected from the natural number group consisting of 2, 3, 4, 5, 6, 7, 8, 9, 10, 11 and 12.

Preferably n is selected from the group consisting of the natural numbers from 4 to 10. In other words, n is selected from the natural number group consisting of 4, 5, 6, 7, 8, 9 and 10.

More preferably n is selected from the group consisting of the natural numbers from 6 to 8. In other words, n is selected from the natural number group consisting of 6, 7 and.

Preferred compounds represented by the formula I and physiologically acceptable salts thereof include but not limit to the compounds shown in IA.

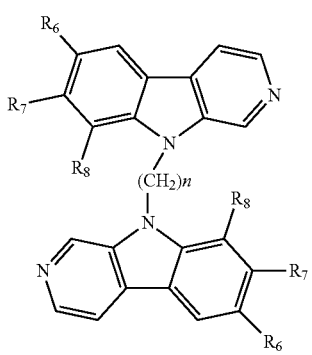

IA $R_6$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, cyano;

$R_7$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, cyano;

$R_8$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, cyano;

Substituents on the substituted or unsubstituted C1-4 linear or branched alkyl are selected from the group consisting of hydroxy, mercapto, amino, aldehyde, carboxyl, carbamoyl, fluoro, chloro, bromo, nitro, and cyano.

Preferred compounds represented by the formula I and physiologically acceptable salts thereof include but not limit to the compounds shown in IB.

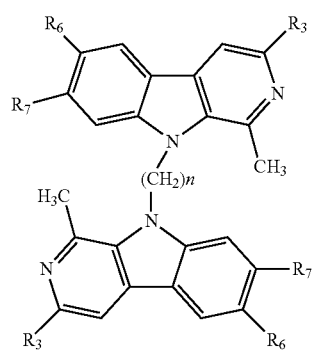

IB $R_3$ is substituent selected from the group consisting of hydrogen, C1-6 alkoxy-CO—, C1-4alkyl-NH—CO—;

$R_6$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, cyano;

$R_7$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, cyano;

Substituents on the substituted or unsubstituted C1-4 linear or branched alkyl are selected from the group consisting of hydroxy, mercapto, amino, aldehyde, carboxyl, carbamoyl, fluoro, chloro, bromo, nitro, and cyano.

Preferred compounds represented by the formula IB and physiologically acceptable salts thereof include but not limit to the compounds shown in IBa.

IBa $R_6$ is substituent selected from the group consisting of hydrogen, nitro, halogen, substituted or unsubstituted C1-4 linear or branched alkyl, hydroxyl, substituted or unsubstituted C1-4 linear or branched alkoxy, mercapto, amino, aldehyde, carboxyl, cyano;

$R_7$ is substituent selected from the group consisting of hydrogen, nitro, halogen, substituted or unsubstituted C1-4 linear or branched alkyl, hydroxyl, substituted or unsubstituted C1-4 linear or branched alkoxy, mercapto, amino, aldehyde, carboxyl, cyano;

Substituents on the substituted or unsubstituted C1-4 linear or branched alkyl are selected from the group consisting of hydroxy, mercapto, amino, aldehyde, carboxyl, carbamoyl, fluoro, chloro, bromo, nitro, and cyano.

Preferred compounds represented by the formula TB and physiologically acceptable salts thereof include but not limit to the compounds shown in IBb.

IBb $R_6$ is substituent selected from the group consisting of hydrogen, nitro, halogen, substituted or unsubstituted C1-4 linear or branched alkyl, hydroxyl, substituted or unsubstituted C1-4 linear or branched alkoxy, mercapto, amino, aldehyde, carboxyl, cyano;

$R_7$ is substituent selected from the group consisting of hydrogen, nitro, halogen, substituted or unsubstituted C1-4 linear or branched alkyl, hydroxyl, substituted or unsubstituted C1-4 linear or branched alkoxy, mercapto, amino, aldehyde, carboxyl, cyano;

Substituents on the substituted or unsubstituted C1-4 linear or branched alkyl are selected from the group consisting of hydroxy, mercapto, amino, aldehyde, carboxyl, carbamoyl, fluoro, chloro, bromo, nitro, and cyano.

Preferred compounds represented by the formula I and physiologically acceptable salts thereof include but not limit to the compounds shown in IC.

IC $R_3$ is substituent selected from the group consisting of hydrogen, C1-6 alkoxy-CO—, C1-4alkyl-NH—CO—;

$R_6$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, cyano;

$R_7$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, cyano;

$R_{11}$ represents one or more substituents, can connect with phenyl at any location which can be connected, and is selected from the group consisting of hydrogen, hydroxyl, mercapto, amino, aldehyde, carboxyl, carbamoyl, halogen, nitro, cyano, C1-4 alkyl, C1-4 alkoxy, C1-4 alkylamino group, C1-4 alkoxy C1-4 alkyl group.

Substituents on the substituted or unsubstituted C1-4 linear or branched alkyl are selected from the group consisting of hydroxy, mercapto, amino, aldehyde, carboxyl, carbamoyl, fluoro, chloro, bromo, nitro, and cyano.

Preferred compounds represented by the formula I and physiologically acceptable salts thereof include but not limit to the compounds shown in ID.

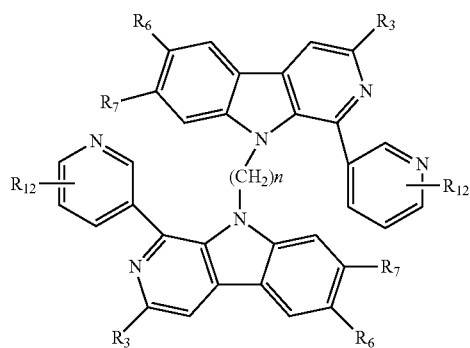

ID

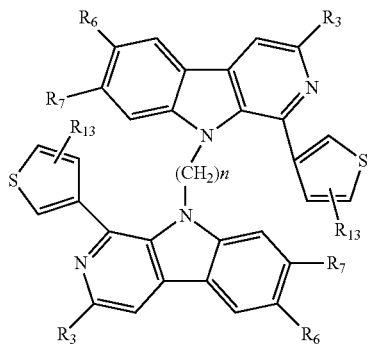

IE $R_3$ is substituent selected from the group consisting of hydrogen, C1-6 alkoxy-CO—, C1-4alkyl-NH—CO—;

$R_6$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, cyano;

$R_7$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, cyano;

$R_{12}$ represents one or more substituents, can connect with pyridine at any location which can be connected, and is selected from the group consisting of hydrogen, hydroxyl, mercapto, amino, aldehyde, carboxyl, carbamoyl, halogen, nitro, cyano, C1-4 alkyl, C1-4 alkoxy, C1-4 alkylamino group, C1-4 alkoxy C1-4 alkyl group.

Substituents on the substituted or unsubstituted C1-4 linear or branched alkyl are selected from the group consisting of hydroxy, mercapto, amino, aldehyde, carboxyl, carbamoyl, fluoro, chloro, bromo, nitro, and cyano.

Preferred compounds represented by the formula I and physiologically acceptable salts thereof include but not limit to the compounds shown in IE.

$R_3$ is substituent selected from the group consisting of hydrogen, C1-6 alkoxy-CO—, C1-4alkyl-NH—CO—;

$R_6$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, cyano;

$R_7$ is substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched alkylamino group wherein the alkylamino group include mono- and bis-alkylamino, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, cyano;

$R_{13}$ represents one or more substituents, can connect with thiophere at any location which can be connected, and is selected from the group consisting of hydrogen, hydroxyl, mercapto, amino, aldehyde, carboxyl, carbamoyl, halogen, nitro, cyano, C1-4 alkyl, C1-4 alkoxy, C1-4 alkylamino group, C1-4 alkoxy C1-4 alkyl group.

Substituents on the substituted or unsubstituted. C1-4 linear or branched alkyl are selected from the group consisting of hydroxy, mercapto, amino, aldehyde, carboxyl, carbamoyl, fluoro, chloro, bromo, nitro, and cyano.

In the present invention, the substituents on the substituted or unsubstituted C1-6 linear or branched alkyl are selected from the group consisting of hydroxyl, mercapto, amino, aldehyde, carboxyl, carbamoyl, halogen, nitro, cyano.

In the present invention, preferably C1-6 linear or branched alkyl are selected from the group consisting of C1-4 linear or branched alkyl or C2-5 linear or branched alkyl, more preferably, C1-6 linear or branched alkyl selected from the group consisting of methyl, ethyl, propyl, isopropyl, butyl, pentyl, isopentyl.
The most preferred compounds are selected from but not limit to the compounds shown in the following table.
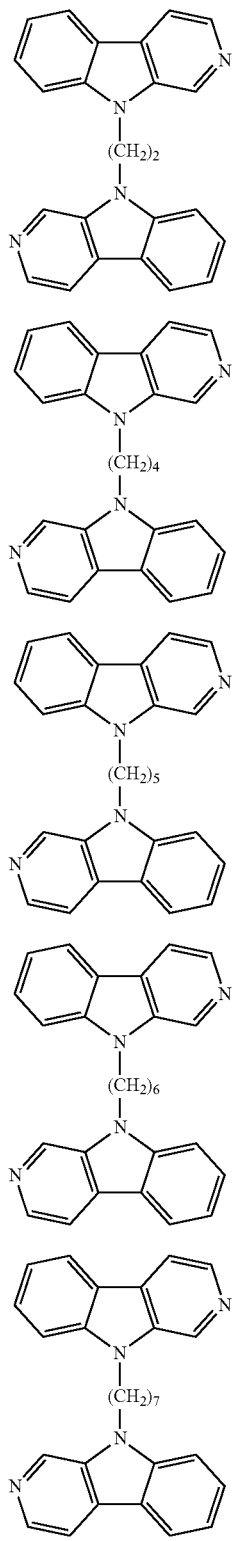
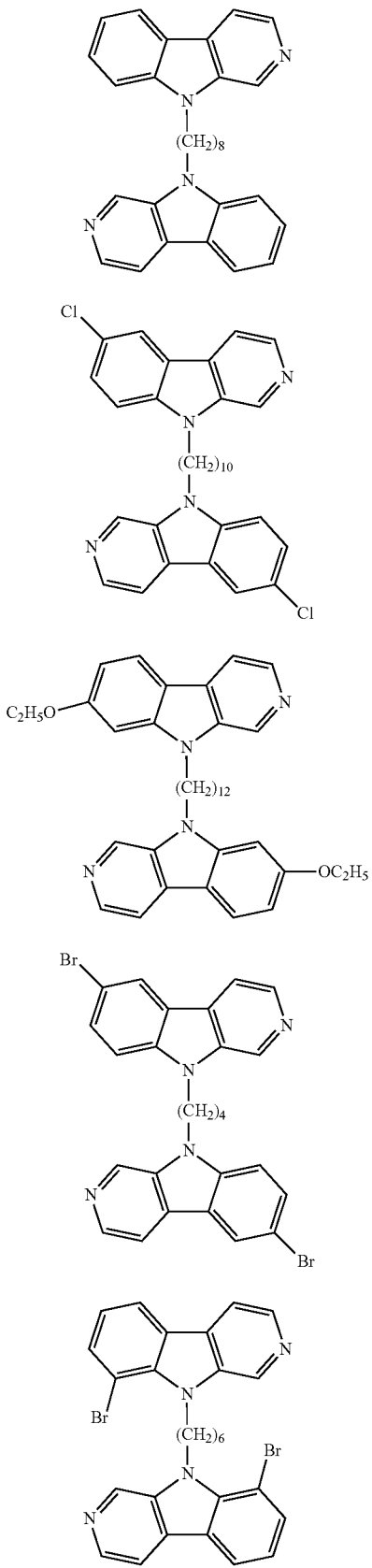

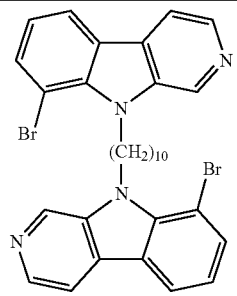
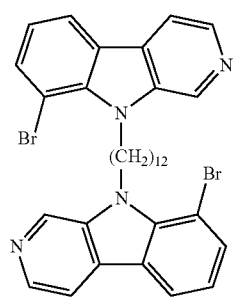
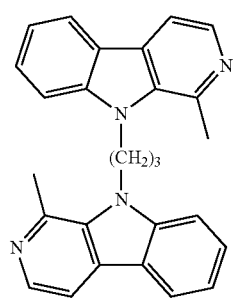
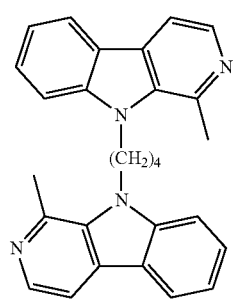
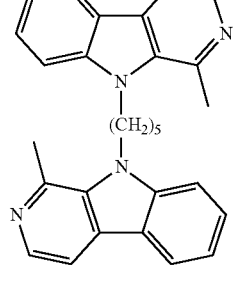
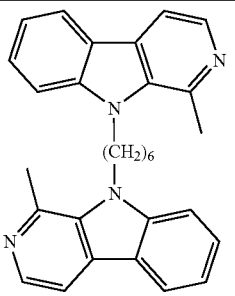
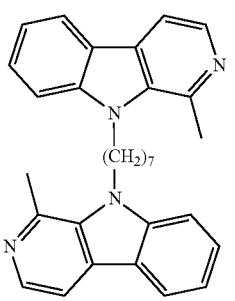
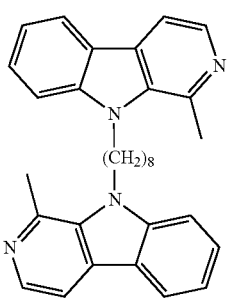
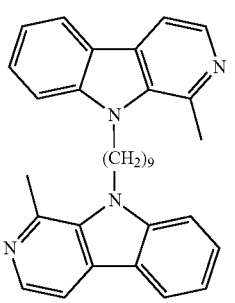
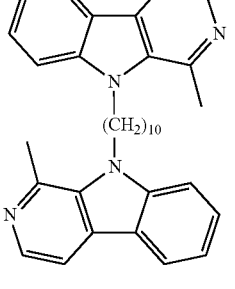

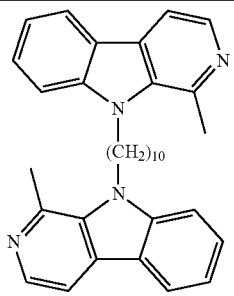
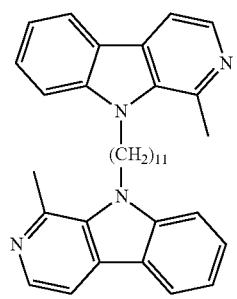
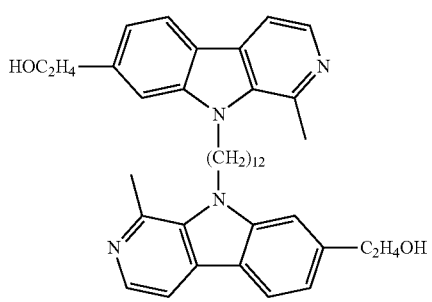
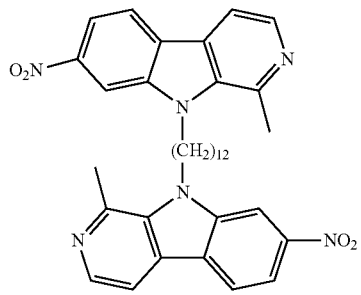
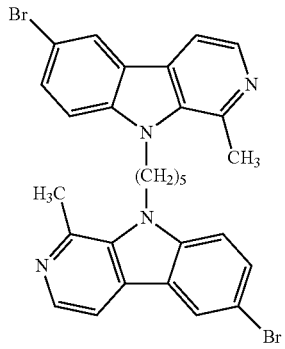
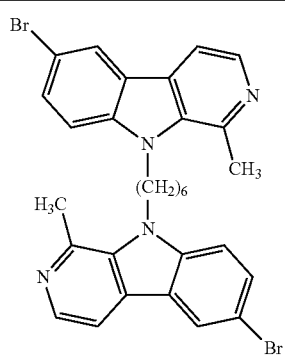
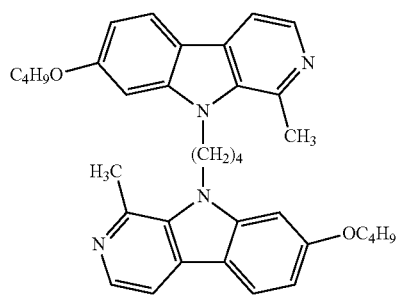
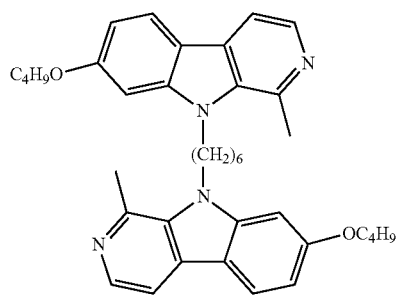
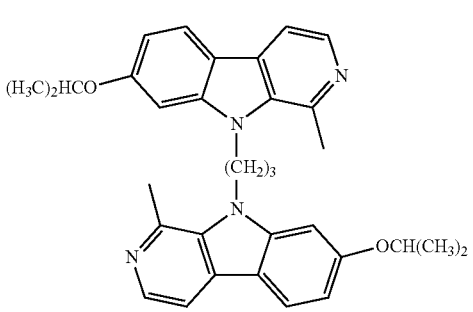
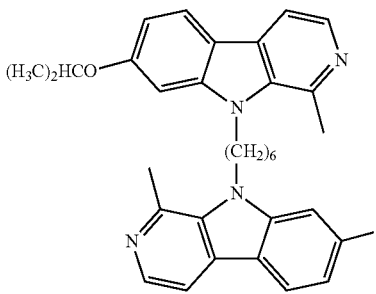

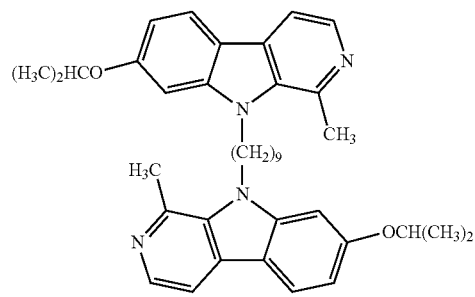
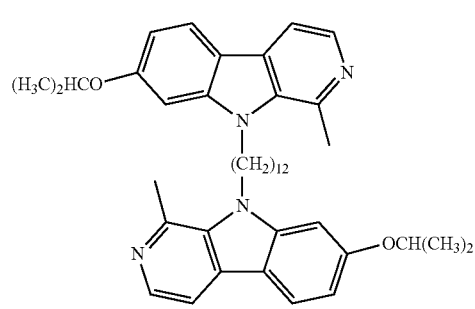
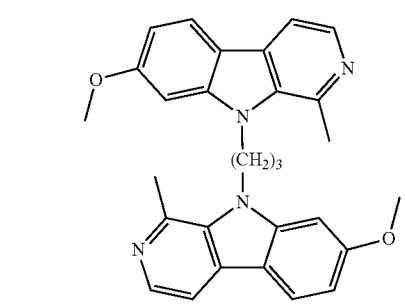
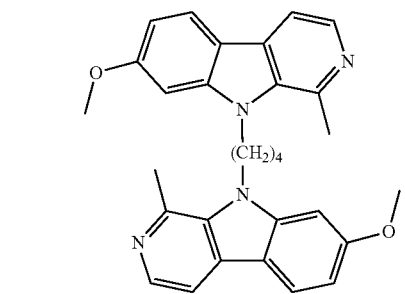
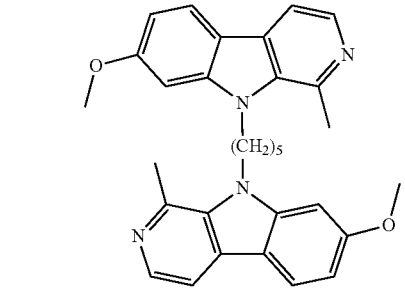
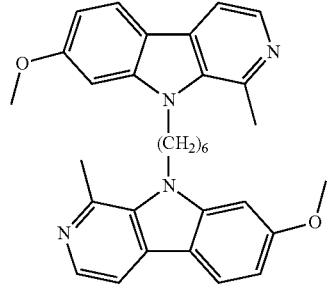
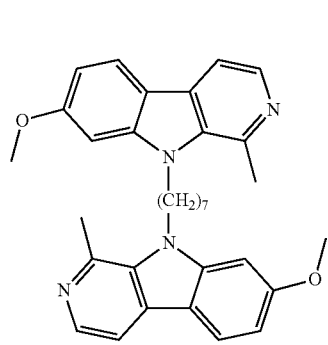
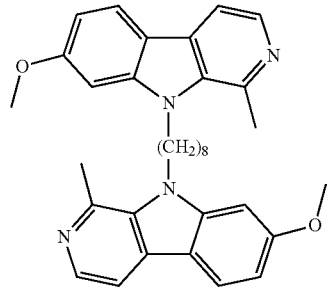
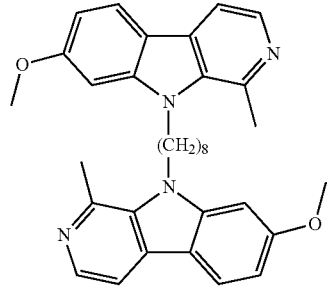
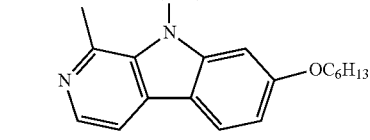

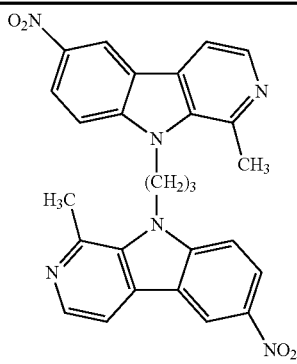
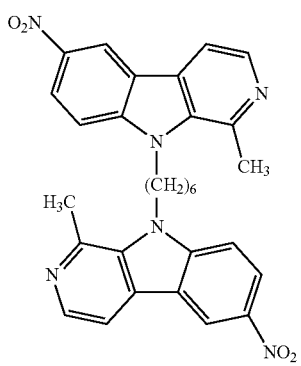
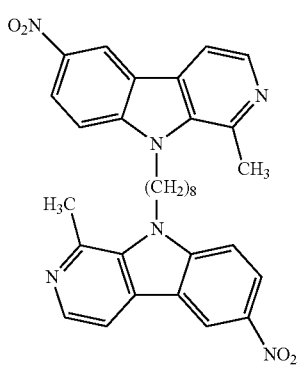
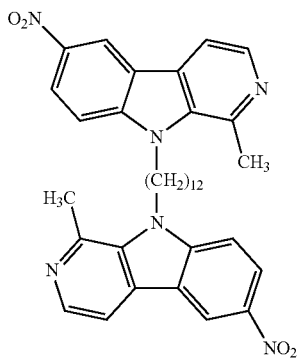
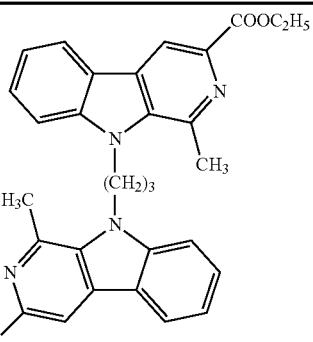
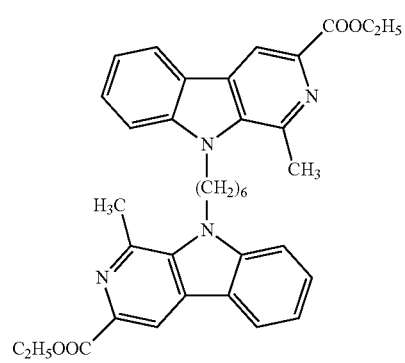
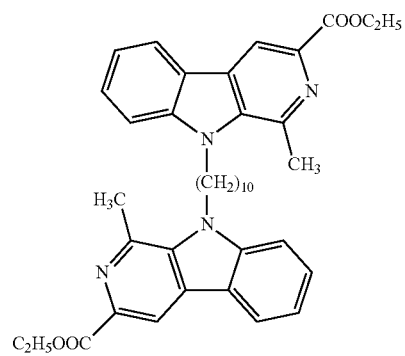
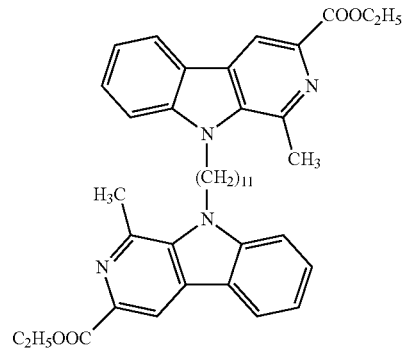

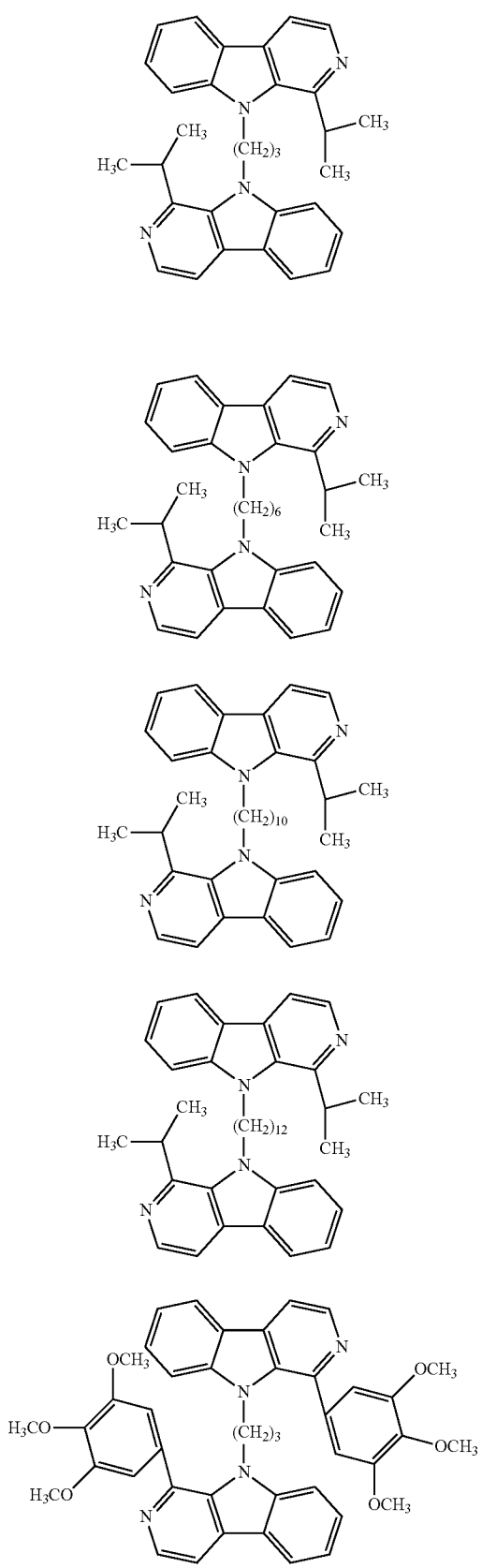
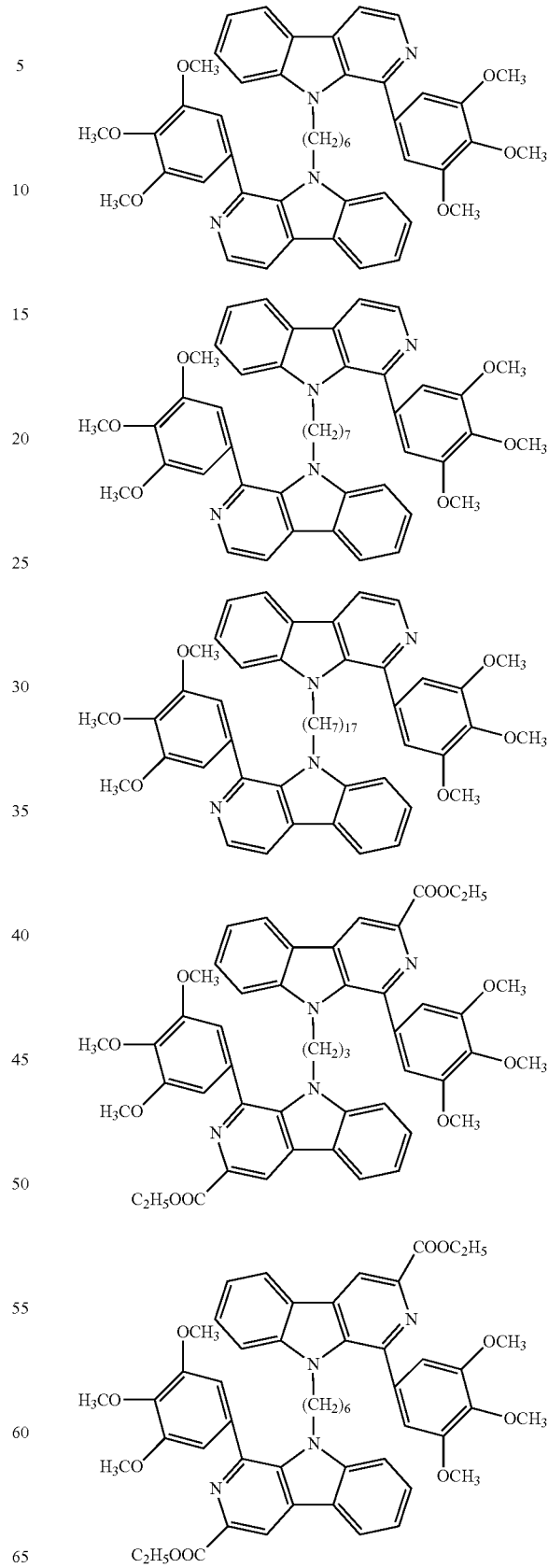

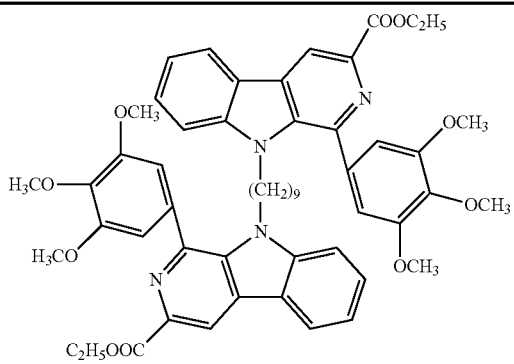
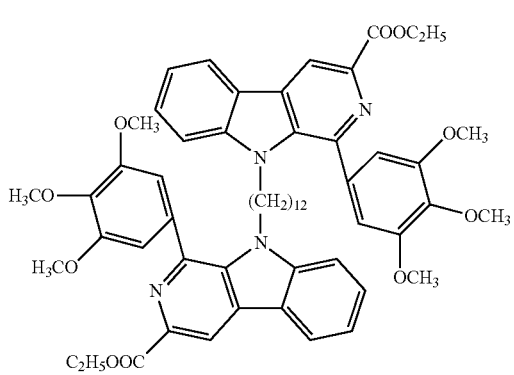
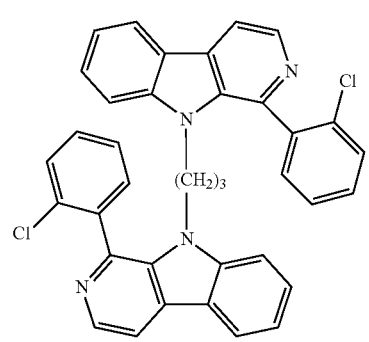
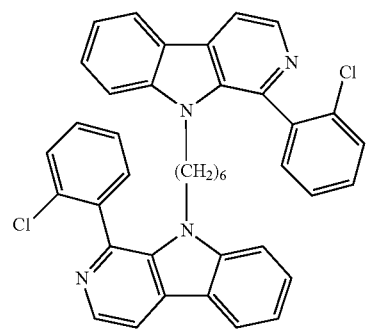
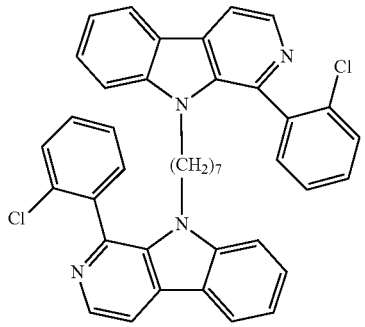
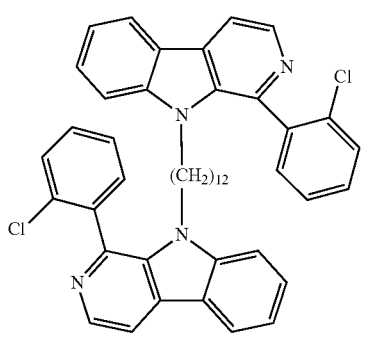
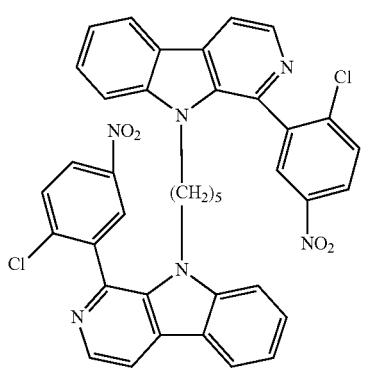
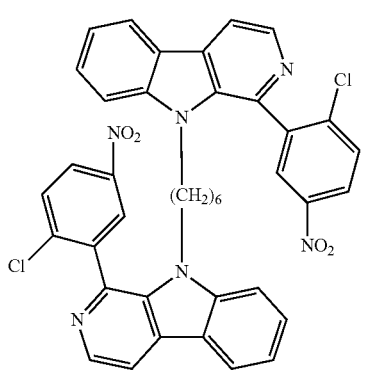

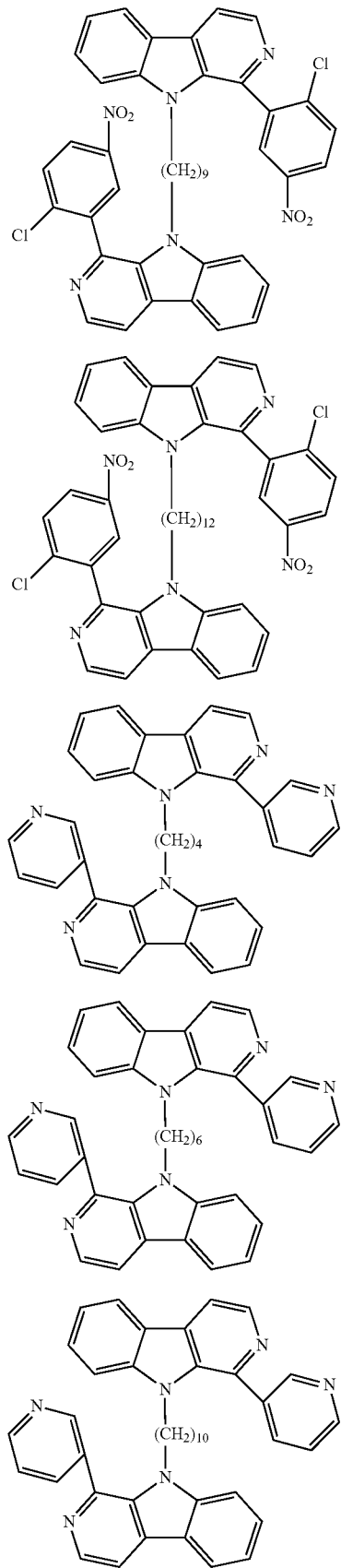
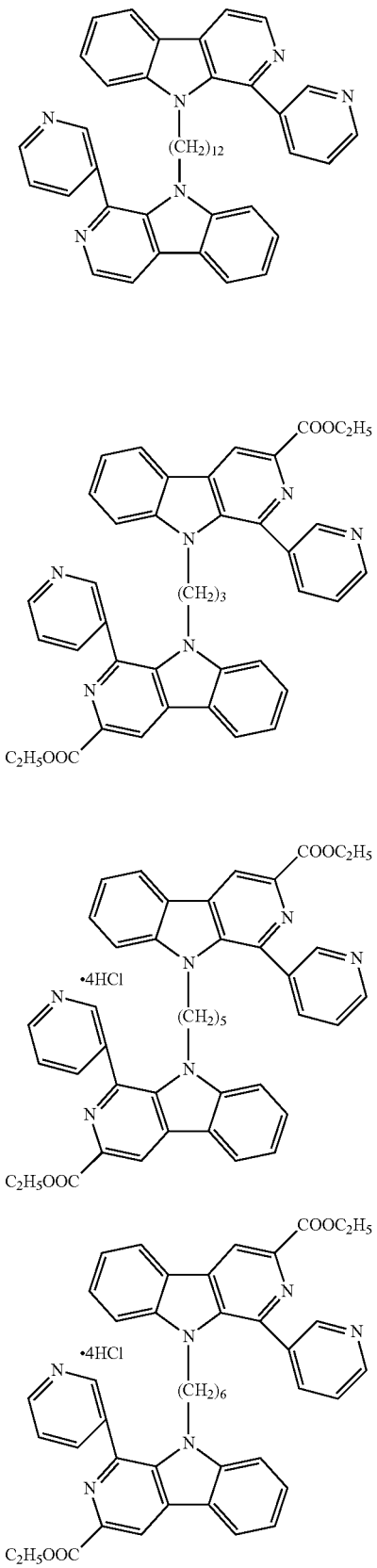

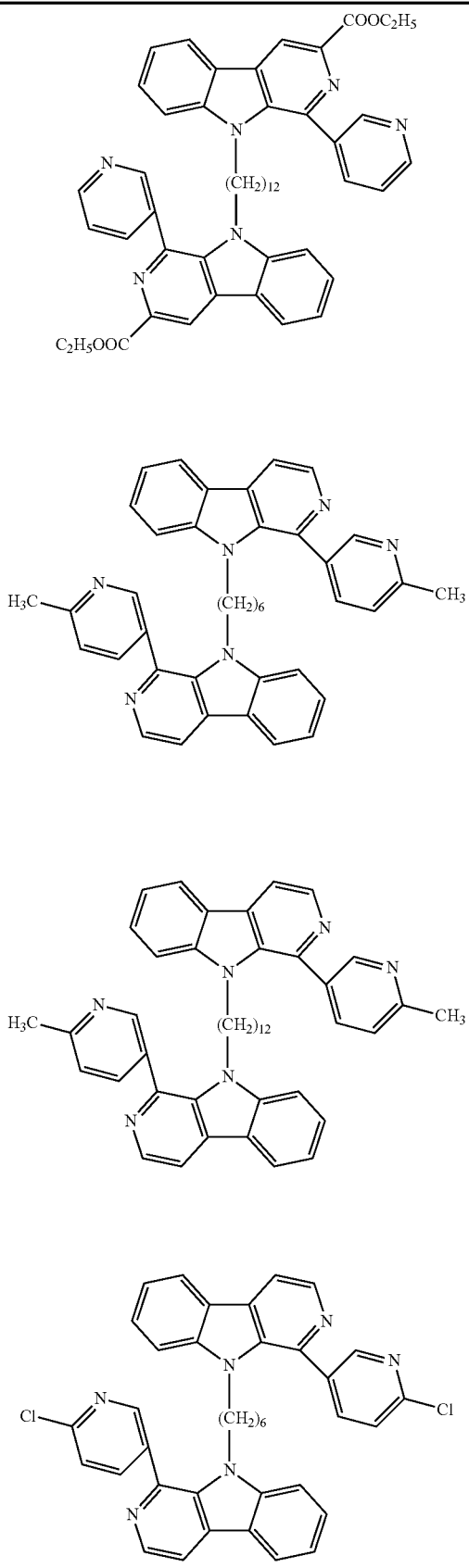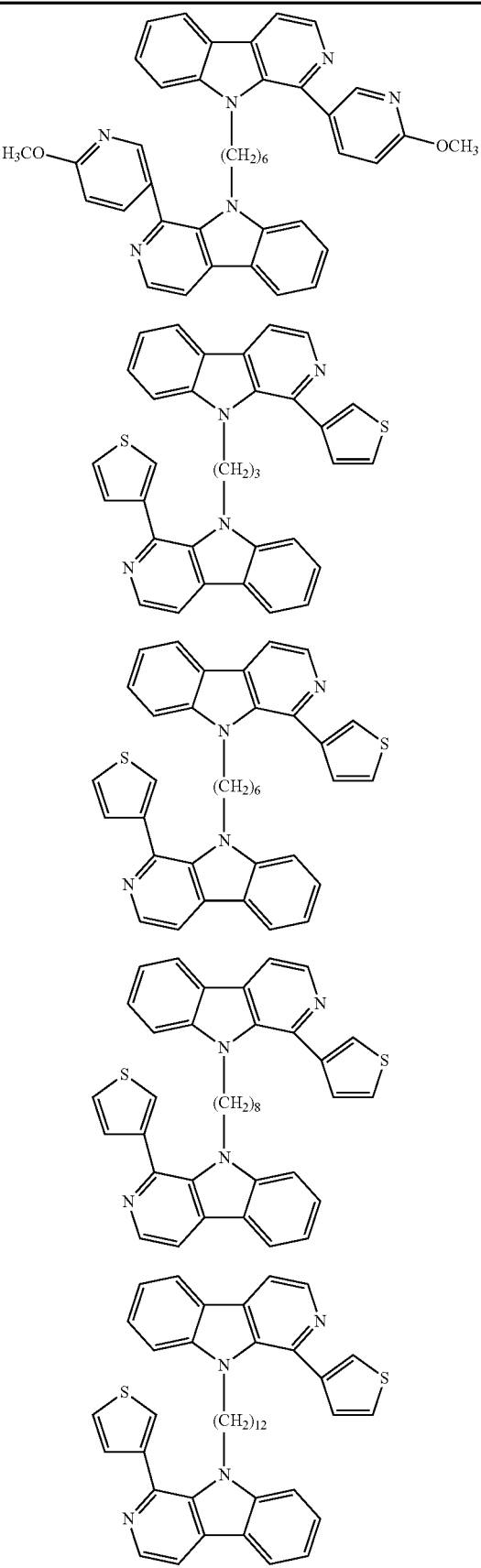

-continued

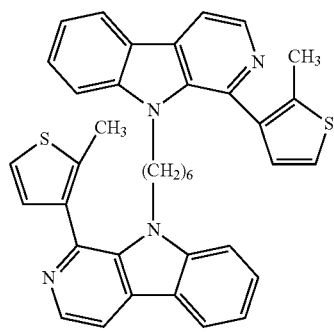

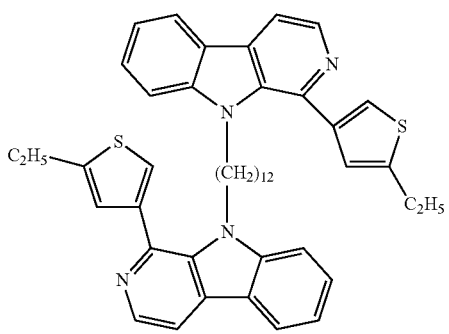

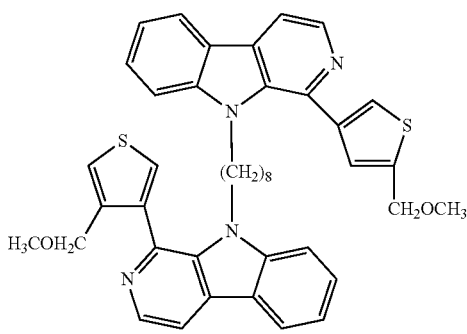

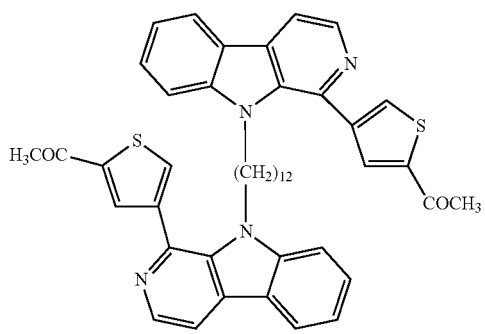

The compounds of this invention can be prepared by the following process, comprising:

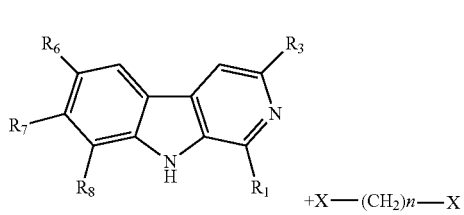

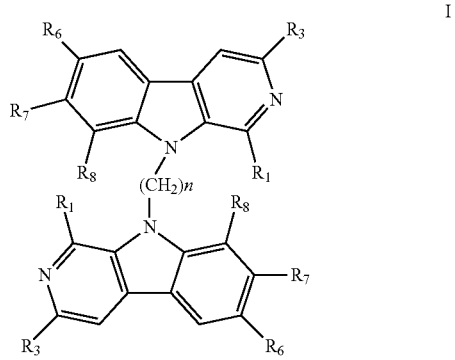

X is halogen; the definition of $R_1$, $R_3$, $R_6$, $R_7$ and $R_8$ are consistent with aforementioned definition;

the β-carboline compound described as general formula I condensed with dihaloalkane to give compounds described as general formula I. Preferably the said condensation reacted under the condition of base. Preferably the said base are selected from the group consisting of NaH, NaOH, $K_2CO_3$ and $K_3PO_4$. Preferably the solvent of condensation are selected from the group consisting of DMF, DMSO.

The present invention also provide the key intermediate described as general formula 1:

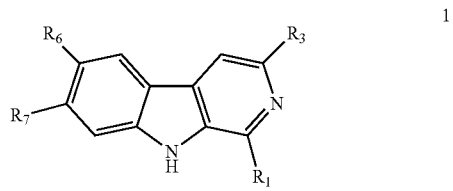

Preferably the key intermediate are selected from the group consisting of

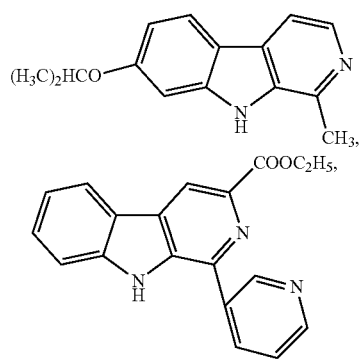

-continued

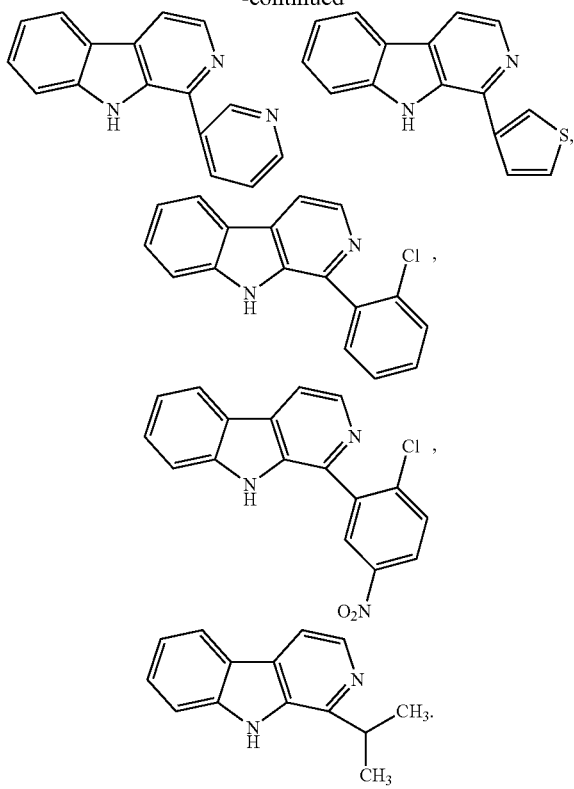

The present invention relates to pharmaceutical compositions containing this invention compounds as the active ingredient. The pharmaceutical compositions can be prepared by methods known in this field. Combining compounds represented by the present invention with one or more pharmaceutically acceptable solid or liquid excipients and/or adjuvants is made into any formulation suitable for human or animal. The weight of the compounds of this invention in pharmaceutical composition accounts for 0.1 to 95%.

Compounds or their pharmaceutical compositions of the present invention can be administered in unit dosage form. The route of administration can be divided into intestinal and parenteral, such as oral, intravenous, intramuscular, subcutaneous, nasal, oral mucosa, eyes, lungs and respiratory tract, skin, vagina, rectum and so on.

Dosage form can be a liquid, a solid or semi-solid dosage forms. Liquid dosage forms can be solutions (including true solutions and colloid solutions), emulsions (including o/w type, w/o type and multiple emulsions), suspensions, injections (including aqueous injections, powder and infusion), eye drops, nasal drops, lotions and liniments etc.; solid dosage forms can be tablets (including conventional tablets, enteric-coated tablets, tablets, dispersible tablets, chewable tablets, effervescent tablets, orally disintegrating tablets), capsules (including hard capsules, soft capsules, enteric capsules), granules, powders, pellets, pills, suppositories, films, patches, gas (powder) aerosols, sprays, etc.; semi-solid dosage forms may be ointments, gels, pastes and the like.

The compounds of this invention can be made into the normal preparation, sustained release formulations, controlled release formulations, targeting formulations and various particulate delivery systems.

In order to making compounds of the invention into tablets, various known excipients can be widely used in this field. Such as diluents, binders, wetting, agents, disintegrants, lubricants and glidants. The diluent can be starch, dextrin, sucrose, glucose, lactose, mannitol, sorbitol, xylitol, microcrystalline cellulose, calcium sulfate, calcium hydrogen phosphate, calcium carbonate, etc.; wetting agents can be water, ethanol, iso-propanol and the like; binder can be starch, dextrin, syrup, honey, glucose solution, microcrystalline cellulose, acacia mucilage, clear glue, sodium carboxymethyl cellulose, methyl cellulose, hydroxypropylmethyl cellulose, ethyl cellulose, acrylic resins, carbomer, polyvinyl pyrrolidone, polyethylene glycol and the like; disintegrating agents can be dry starch, microcrystalline cellulose, low-substituted hydroxypropyl cellulose, cross-linked poly vinyl pyrrolidone, cross-linked sodium carboxymethyl cellulose, sodium carboxymethyl starch, sodium bicarbonate and citric acid, polyoxyethylene sorbitan fatty acid esters, sodium lauryl sulfate and the like; lubricants and glidants agent can be talc, silicon dioxide, stearate, tartaric acid, liquid paraffin, polyethylene glycol and the like.

The tablets can be further made into tablets, such as sugar-coated tablets, film-coated tablets, enteric coated tablets, or double tablets and multilayer tablets.

In order to making dosing unit into capsules, the active ingredients of the present invention compounds combine with diluent and glidants, the mixture was directly put into a hard capsule or soft capsule. With diluent, binder, disintegrant, the active ingredients of the present invention compounds can be made into granules or pellets, then place into a hard gelatin capsules or soft capsules. The species of diluen, adhesives, wetting agents, disintegrants, glidants used for the preparation of tablets of the present invention compounds can also be applied for preparing capsules of the present invention compounds.

In order to making compounds of the invention into injection, water, ethanol, isopropanol, propylene glycol or their mixture can be used as solvent, the common and appropriate amount of solubilizer, co-solvents, pH regulating agents, osmotic pressure adjusting agent can be added in the field. Solubilizers or co-solvents can be poloxamer, lecithin, hydroxypropyl-β-cyclodextrin; pH regulating agent can be a phosphate, acetate, hydrochloric acid, sodium hydroxide and so on; osmotic pressure regulating agent can be sodium chloride, mannitol, glucose, phosphate, acetate and the like. Mannitol and glucose can be added as proppant when freeze-dried powders need to be prepared.

In addition, if desired, coloring agents, preservatives, perfumes, flavoring agents or other additives to pharmaceutical formulations can be added.

To achieve the purpose of treatment and enhance the therapeutic effect, the drug or pharmaceutical composition of this present invention can be administered by any known methods of administration.

The compounds of the invention may be used to prepare anti-tumor drugs. The tumors include, but are not limited to, melanoma, stomach cancer, lung cancer, breast cancer, renal cancer, liver cancer, Oral epidermoid carcinoma, cervical cancer, ovarian cancer, pancreatic cancer, prostate cancer, colon cancer. Said stomach cancer include gastric adenocarcinoma; said lung cancer include lung adenocarcinoma; said colon cancer include colonic adenocarcinoma; said ovarian cancer include ovarian adenocarcinoma.

Dose of the pharmaceutical composition of the present invention compounds can be varied in a wide range according to the property and severity of prevention or treatment of the diseases, individual situation of patients or animals and the administration and the formulation. In general, a suitable daily dosage range for the present invention compounds is 0.001-150 mg/Kg weight, preferably 0.1-100 mg/Kg weight, more preferably 1-60 mg/Kg weight, and most preferably 2-30 mg/Kg weight. The above dosage can be one unit or be divided into several administered dosage units, depending on the doctor's clinical experience and the use of other therapeutic regimen.

The compounds or their compositions of the invention can be administered alone, or in combination with other therapeutic drugs or symptomatic drugs. When the compounds of the present invention have synergistic effects with other therapeutic agents, their dosage should be adjusted according to the actual situation.

DETAILED EXAMPLES

The present disclosure is further illustrated by the following examples of synthesis of bis-β-carboline thereof. Those skilled in the art should understand that these examples are merely for illustrative purposes, without limiting the scope of the present invention. The scope of the present invention is limited only by the claims. Under conditions without departing from the scope of the claims, people skilled in the art can modify or improve aspects of the present invention, such modifications and improvements also belong to the scope of protection of the present invention.

Also, unless otherwise specified, materials and the reagents used in the following examples are those commonly used in the field, which can be commercially available; the intermediates used can be commercially available or prepared by known methods; methods used are conventional methods known by those skilled in the art.

PREPARATION EXAMPLE

Preparation Example 1

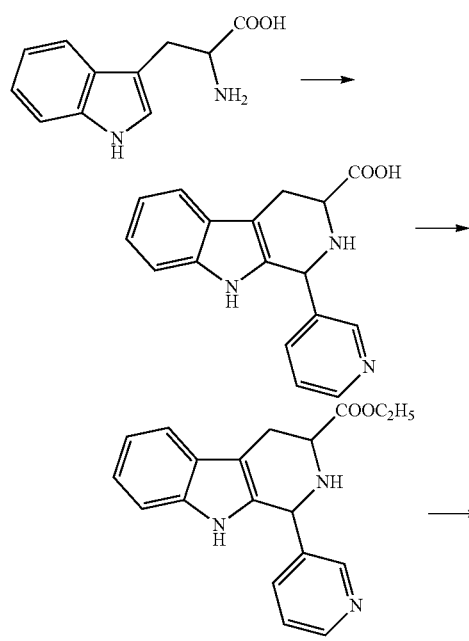

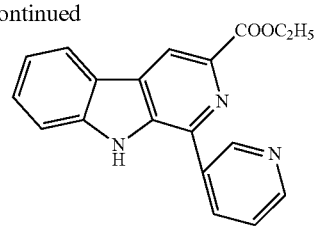

ethyl 1-(pyridin-3-yl)-β-carboline-3-carboxylate (a) Synthesis of ethyl 1-pyridin-3-yl)-1,2,3,4-tetrahydro-β-carboline-3-carboxylate L-tryptophan ethyl ester (8.04 g, 30 mmol) and isopropanol (84 mL) were added in 250 ml round-bottomed flask, the reaction mixture was stirred at room temperature until the solution was clear, 3-Pyridinecarboxaldehyde (36 mmol) was added followed and the reaction mixture was heated at reflux temperature, TLC detection until the reaction completed. The reaction mixture was concentrated under reduced pressure to give light yellow solid, which was dissolved in water and then alkalized with $NaHCO_3$. The solution was extracted with $CH_3COOC_2H_5$. The extract liquor was merged extract liquor, washed with water and saturated brine, then dried with anhydrous $NaSO_4$, the solvent was removed under reduced pressure to give oil product, which could directed be used to the next step without purification.

(b) Synthesis of ethyl 1-(pyridin-3-yl)-β-carboline-3-carboxylate

A solution of the previous oil and sulfur (3.2 g) in xylene (100 ml) was heated at reflux temperature. TLC detection until the reaction completed. On cooling to room temperature the reaction mixture was put followed in the refrigerator at 4° C. for 2 h, the yellow precipitate formed and filtered, washed thoroughly with petroleum ether. The precipitate was dissolved in ethanol and stirred at reflux temperature for 1 h with activated carbon, then filtered, washed several times with hot ethanol. on cooling, the precipitated flocks were filtered off, washed with ether, and dried to give light yellow solid (8.2 g, 86% yield). $^1$H NMR (300 MHz, $CDCl_3$): δ 11.6 (1H, s), 9.48 (1H, s), 8.91 (1H, s), 8.52-8.54 (1H, m), 8.42-8.45 (1H, m), 8.23 (1H, d, J=7.8 Hz), 7.58 (2H, d, J=3.9 Hz), 7.43-7.48 (1H, m), 7.35-7.40 (1H, m), 4.55 (2H, q, J=7.2 Hz), 1.52 (3H, t, J=7.2 Hz); $^{13}$C NMR (75 MHz, DMSO): δ 165.9, 150.3, 149.6, 142.0, 139.8, 137.7, 136.9, 135.2, 133.9, 130.0, 129.5, 124.6, 122.6, 121.6, 121.2, 117.7, 113.3, 61.5, 15.2; ESI-MS m/z: 318.1.

Preparation Example 2

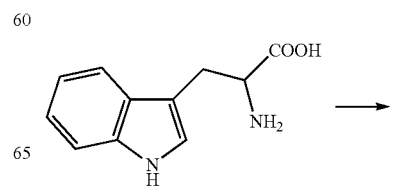

-continued

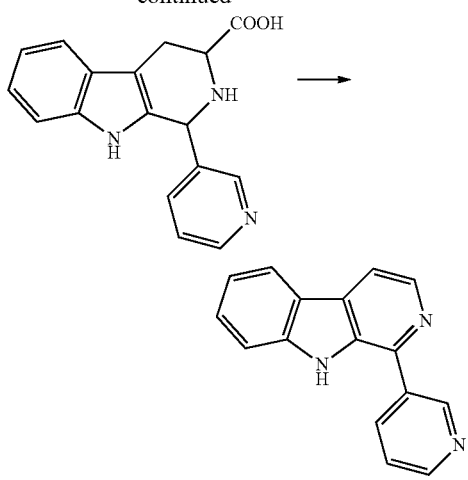

1-(pyridin-3-yl)-β-carboline

L-Tryptophan (10 mmol) was dissolved in acetic acid (20 ml), the reaction mixture was heated until the solution was clear, then 3-pyridinecarboxaldehyde (10.6 mmol) was added, the reaction mixture was heated at reflux temperature, TLC detection until the reaction completed. The reaction mixture was poured into boiling water, potassium dichromate (20 mmol) was added, The reaction mixture was heated continued for 20 min, On cooling to room temperature anhydrous $Na_2SO_3$ (2.7 g) was added at stirring, the solution was adjusted pH value to about 10 with the solid of NaOH and extracted with $CH_3COOC_2H_5$. The extract liquor was merged extract liquor, washed with water and saturated brine, then dried with anhydrous $Na_2SO_4$, the solvent was removed under reduced pressure to give yellow solid, which crystallized from $CH_3COOC_2H_5$. light yellow crystals (1.97 g, 80% yield). $^1H$ NMR (300 MHz, $CDCl_3$): δ 10.11 (1H, s), 9.39 (1H, d, J=1.8 Hz), 8.65 (1H, dd, J=1.8 Hz, 4.5 Hz), 8.61 (1H, d, J=5.4 Hz), 8.38-8.42 (1H, m), 8.18 (1H, d, J=7.8 Hz), 8.04 (1H, d, J=5.4 Hz), 7.52-7.61 (3H, m), 7.30-7.36 (1H, m); $^{13}C$ NMR (75 MHz, DMSO): δ 149.9, 149.5, 141.7, 139.8, 139.2, 136.5, 134.6, 133.8, 130.1, 129.1, 124.5, 122.3, 121.3, 120.4, 115.1, 113.0; ESI-MS m/z: 246.2.

Preparation Example 3

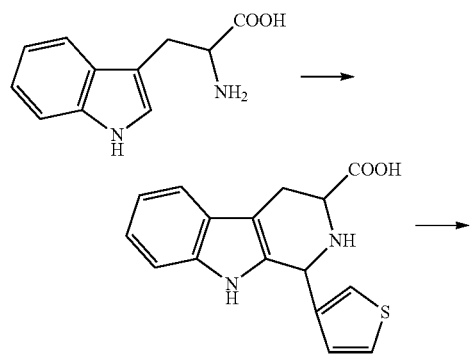

-continued

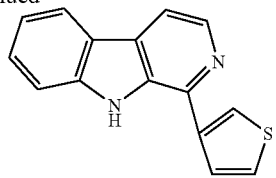

1-(thiophene-3-yl)-β-carboline

To a stirred solution of L-Tryptophan (10 mmol) in $CH_2Cl_2$ (100 ml) at room temperature, phenylacetaldehyde (1.05 ml) and trifluoroacetic acid (1.5 ml) were added and the reaction mixture was stirred continually at room temperature, TLC detection until the reaction completed. The reaction mixture was concentrated under reduced pressure to remain about 30 ml and filtered, washed carefully with ether to give the solid. The solid was dissolved in acetic acid followed by addition of $KMnO_4$ (30 mmol). The reaction mixture was heated at reflux temperature, TLC detection until the reaction completed. The solvent was concentrated under reduced pressure to give the residual, which was poured into water and then alkalized with $NaHCO_3$. The solution was extracted with $CH_3COOC_2H_5$. The extract liquor was merged extract liquor, washed with water and saturated brine, then dried with anhydrous $Na_2SO_4$ and decolorized with activated carbon, the solvent was filtered and removed under reduced pressure to give crude product, which was purified vis silica gel column chromatography (eluent: $CH_3COOC_2H_5$). The eluent target product was collected, concentrated under reduced pressure to give yellow solid (2.1 g, 83% yield). $^1H$ NMR (300 MHz, $CDCl_3$): δ 8.77 (1H, s), 8.47 (1H, d, J=5.1 Hz), 8.11 (1H, d, J=8.1 Hz), 7.87 (2H, d, J=5.1 Hz), 7.74-7.75 (1H, m), 7.53-7.55 (2H, m), 7.47-7.49 (1H, m), 7.28-7.33 (1H, m), 7.19-7.22 (1H, m); $^{13}C$ NMR (75 MHz, DMSO): δ 144.2, 141.7, 138.7, 137.1, 131.4, 130.4, 129.1 (2C), 128.6, 126.4, 122.1, 121.4, 120.6, 114.5, 113.2; EST-MS m/z: 251.1.

Preparation Example 4

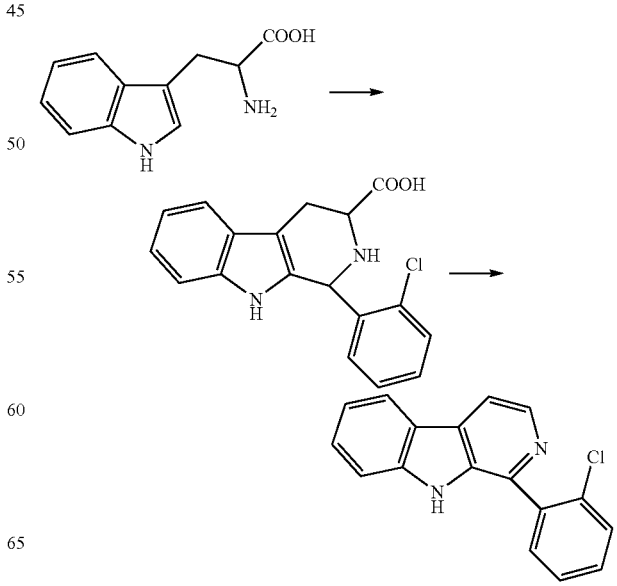

1-(2-chlorophenyl)-β-carboline

L-Tryptophan (10 mmol) was dissolved in acetic acid (20 ml), the reaction mixture was heated until the solution was clear, then 2-chloro-benzaldehyde (10.6 mmol) was added, the reaction mixture was heated at reflux temperature, TLC detection until the reaction completed. The reaction mixture was poured into boiling water, potassium dichromate (20 mmol) was added, The reaction mixture was heated continued for 20 min, On cooling to room temperature anhydrous $Na_2SO_3$ (2.7 g) was added at stirring, the solution was adjusted pH value to about 10 with the solid of NaOH and extracted with $CH_3COOC_2H_5$. The extract liquor was merged extract liquor, washed with water and saturated brine, then dried with anhydrous $Na_2SO_4$, the solvent was removed under reduced pressure to give white solid, which crystallized from $CH_3COOC_2H_5$ to give pure product (1.38 g, 50% yield). $^1$H NMR (300 MHz, CDCl$_3$): δ 8.55 (1H, d, 0.1=5.1 Hz), 8.29 (1H, s), 8.14-8.19 (1H, m), 8.00 (1H, dd, J=0.6 Hz, 5.4 Hz), 7.51-7.62 (3H, m), 7.39-7.46 (3H, m), 7.27-7.33 (1H, m); $^{13}$C NMR (75 MHz, DMSO): δ 141.9, 141.4, 138.4, 137.8, 134.4, 133.1, 132.5, 130.9, 130.4, 128.9 (2C), 128.0, 122.4, 121.3, 120.1, 115.1, 112.8; ESI-MS 279.1.

Preparation Example 5

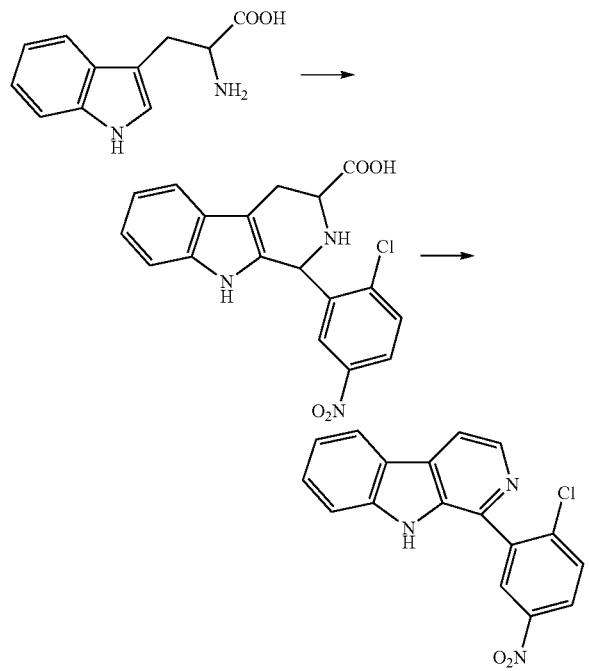

1-(2-chloro-5-nitro-phenyl)-β-carboline

L-Tryptophan (10 mmol) was dissolved in acetic acid (20 ml), the reaction mixture was heated until the solution was clear, then 2-chloro-5-nitro-benzaldehyde (10.3 mmol) was added, the reaction mixture was heated at reflux temperature for 50 minutes, TLC detection until the reaction completed. The reaction mixture was poured into boiling water, potassium dichromate (5.0 g) was added, The reaction mixture was heated continued for 10 min, On cooling to room temperature anhydrous $Na_2SO_3$ (4.0 g) was added at stirring, the solution was adjusted pH value to about 10 with the solid of NaOH and extracted with $CH_3COOC_2H_5$. The extract liquor was merged extract liquor, washed with water and saturated brine, then dried with anhydrous $Na_2SO_4$, the solvent was removed under reduced pressure to give yellow solid, (1.62 g, 50% yield). $^1$H NMR (300 MHz, CDCl$_3$): δ 8.57 (1H, d, J=5.1 Hz), 8.51 (1H, d, 0.1=2.7 Hz), 8.25 (1H, dd, J=2.7 Hz, 8.7 Hz), 8.18 (1H, d, J=7.8 Hz), 8.08 (1H, d, J=5.1 Hz), 7.72 (1H, d, J=8.7 Hz), 7.55-7.61 (1H, m), 7.50 (1H, d, J=7.8 Hz), 7.32-7.37 (1H, m); $^{13}$C NMR (75 MHz, CDCl$_3$): δ 147.0, 141.4, 140.3, 139.5, 138.8, 138.6, 134.4, 132.0, 129.5, 129.3, 127.2, 125.5, 122.5, 121.2, 120.3, 115.8, 112.6; ESI-MS m/z: 324.1.

Preparation Example 6

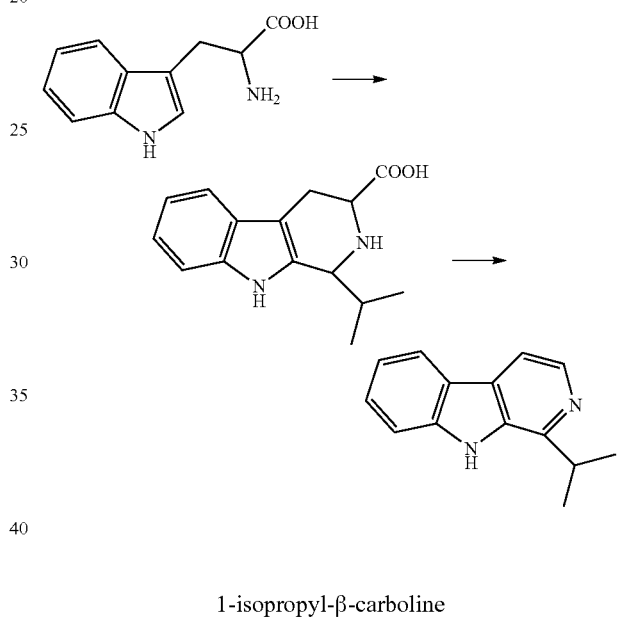

1-isopropyl-β-carboline

L-Tryptophan (10 mmol) was dissolved in acetic acid (20 ml), the reaction mixture was heated until the solution was clear, then isobutylaldehyde (10.3 mmol) was added, the reaction mixture was heated at reflux temperature, TLC detection until the reaction completed. The reaction mixture was poured into boiling water, potassium dichromate (7.6 g) was added, The reaction mixture was heated continued for 5 min, On cooling to room temperature anhydrous $Na_2SO_3$ (14.8 g) was added at stirring, the solution was adjusted pH value to about 10 with the solid of NaOH and extracted with $CH_3COOC_2H_5$. The extract liquor was merged extract liquor, washed with water and saturated brine, then dried with anhydrous $Na_2SO_4$, the solvent was removed under reduced pressure to give white solid, (6.8 g, 67% yield). $^1$H NMR (300 MHz, CDCl$_3$): δ 8.50 (1H, s), 8.43 (1H, d, J=5.4 Hz), 8.12 (1H, d, J=7.8 Hz), 7.82 (1H, d, J=5.4 Hz), 7.52-7.54 (2H, m), 7.27-7.30 (1H, m), 3.45-3.59 (1H, m), 1.52 (3H, s), 1.49 (3H, s); $^{13}$C NMR (75 MHz, CDCl$_3$): δ 150.8, 140.7, 138.5, 133.8, 129.1, 128.4, 122.2, 121.9, 120.1, 113.2, 111.9, 32.4, 22.0; ESI-MS m/z: 211.1.

Preparation Example 7

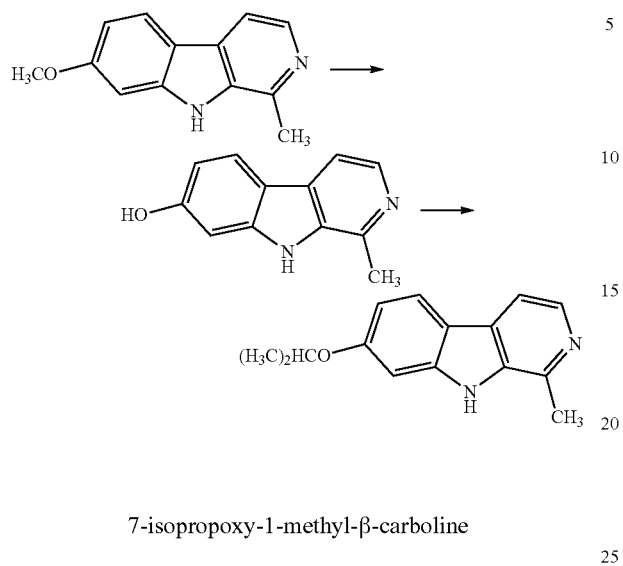

7-isopropoxy-1-methyl-β-carboline (a) Synthesis of 7-hydroxyl-1-methyl-β-carboline A solution of harmine (4.24 g, 20 mmol), 40% hydrobromic acid (45 ml) and acetic acid (30 ml) was heated at reflux temperature in 100 ml round-bottomed flask. TLC detection until the reaction completed. On cooling to room temperature acetone was added (75 ml), the reaction mixture was put in the refrigerator at 4° C. for 2 h, filtered and washed with acetone to give yellow solid, which was dissolved in water and adjusted pH value to 8 with $NaHCO_3$. the precipitated white solid was filtered, washed with water, and dried to give grey white solid (3.7 g, 93% yield).

(b) Synthesis of 7-isopropoxy-1-methyl-β-carboline 7-hydroxyl-1-methyl-β-carboline (1.98 g, 10 mmol) acetone (60 ml) and tripotassium phosphate (4.2 g, 20 mmol) were added followed in 100 ml round-bottomed flask. The reaction mixture was heated at reflux temperature, TLC detection until the reaction completed. The reaction mixture was poured into 200 ml cooled water and extracted with $CH_3COOC_2H_5$. The extract liquor was merged extract liquor, washed with water and saturated brine, then acidified with concentrated hydrochloric acid. The solvent was removed under reduced pressure to give yellow solid, which was dissolved in 100 ml water, then alkalized with $NaHCO_3$. The solution was extracted with $CH_3COOC_2H_5$. The extract liquor was merged extract liquor, washed with water and saturated brine, then dried with anhydrous $Na_2SO_4$, the solvent was removed under reduced pressure to give white solid (2.1 g, 87% yield). $^1H$ NMR (300 MHz, $CDCl_3$): 8.58 (1H, s), 8.29 (1H, d, J=5.4 Hz), 7.94 (1H, d, J=8.7 Hz), 7.71 (1H, d, J=5.4 Hz), 6.95 (1H, d, J=2.1 Hz), 6.87 (1H, dd, J=2.1 Hz, 8.7 Hz), 4.58-4.70 (1H, m), 2.81 (3H, s), 1.41 (3H, s), 1.39 (3H, s); $^{13}C$ NMR (75 MHz, $CDCl_3$): δ 158.8, 142.5, 141.8, 138.2, 135.1, 128.0, 123.3, 115.4, 112.6, 110.9, 97.4, 70.3, 22.6, 21.0; ESI-MS m/z: 241.2.

EXAMPLE

Example 1

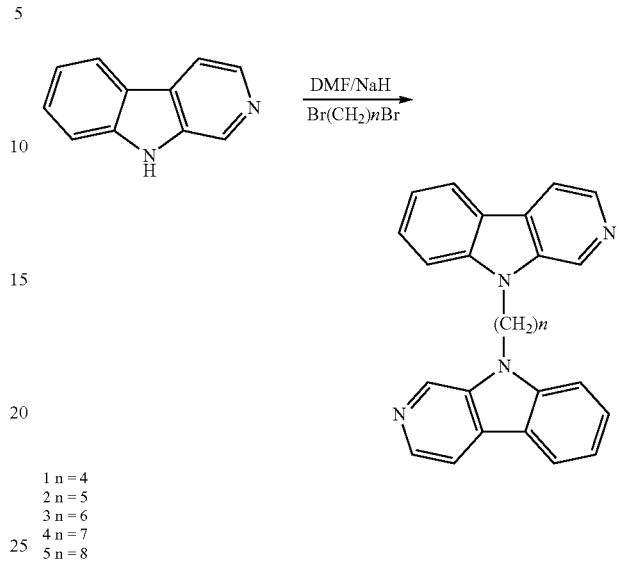

1 n = 4
2 n = 5
3 n = 6
4 n = 7
5 n = 8

Synthesis Process of the bis-β-carboline Compounds (1-4)

β-carboline (2 mmol), 60% NaH (5 mmol), DMF (30 ml) and dihalogenated alkane (1 mmol) were mixed, the reaction mixture was stirred at 60° C. for 8-20 h, TLC detection (eluent:methanol) until the reaction completed. The reaction mixture was poured into 100 ml water and extracted with $CH_2Cl_2$. The extract liquor was merged extract liquor, washed with water and saturated brine, then dried with anhydrous $NaSO_4$, the solvent was removed under reduced pressure to give crude product, which was purified vis silica gel column chromatography ($CH_2Cl_2/CH_3OH$ (v/v)=50:1). The eluent containing target product was collected, concentrated under reduced pressure to give the title compound (white solid)

1,4-bis(β-carboline-9-yl) butane (1)

46% yield, mp >270° C.; IR (KBr) 3041, 2940, 1622, 1556, 1467, 1445, 1328, 1247, 1025, 819, 750, 730; $^1H$-NMR (500 MHz, DMSO-$d_6$) δ 9.03 (2H, s), 8.36 (2H, d, J=5.0 Hz), 8.23 (2H, d, J=8.0 Hz), 8.09 (2H, d, J=5.0 Hz), 7.65 (2H, d, J=8.5 Hz), 7.56 (2H, t, J=7.5 Hz), 7.25 (2H, t, J=7.5 Hz), 4.49 (4H, t, J=7.5 Hz), 1.87-1.92 (4H, m); $^{13}C$ NMR (100 MHz, $CDCl_3$): 141.0, 139.0, 136.4, 131.8, 128.5, 122.0, 121.1, 119.8, 114.7, 109.3, 43.0, 27.0. ESI-MS ink: 391.3 (M).

1,5-bis(β-carboline-9-yl)pentane (2)

27% yield. mp 191-192° C. $^1H$ NMR (500 MHz, $CDCl_3$): 8.82 (2H, s), 8.47 (2H, d, J=5.0 Hz), 8.13 (2H, d, J=7.5 Hz), 7.95 (2H, d, J=5.0 Hz), 7.56 (2H, t, J=7.5 Hz), 7.35 (2H, d, J=8.0 Hz), 7.28 (2H, t, J=7.5 Hz), 4.30 (4H, t, J=7.0 Hz), 1.88-1.94 (4H, m), 1.42-1.47 (2H, m); $^{13}C$ NMR (100 MHz, $CDCl_3$): δ 141.0, 138.9, 136.3, 131.8, 128.3, 128.2, 121.8, 121.0, 119.6, 114.5, 109.2, 43.0, 28.9, 25.1; ESI-MS m/z: 404.9 (M$^+$).

1,6-bis(β-carboline-9-yl) hexane (3)

52% yield. mp 114-115° C. ¹H NMR (300 MHz, CDCl₃): δ 8.83 (2H, s), 8.45 (2H, d, J=5.0 Hz), 8.12 (2H, d, J=8.0 Hz), 7.94 (2H, d, J=5.0 Hz), 7.53-7.56 (2H, m), 7.36 (2H, d, J=8.0 Hz), 7.26-7.28 (2H, m), 4.31 (4H, t, J=7.5 Hz), 1.82-1.87 (4H, m), 1.35-1.38 (4H, m); ¹³C NMR (100 MHz, CDCl₃): δ 140.9, 138.8, 136.3, 131.9, 128.4, 128.2, 121.8, 120.9, 119.4, 114.4, 109.2, 43.0, 28.9, 26.9; ESI-MS m/z: 418.9 (M).

1,7-bis(11-carboline-9-yl) heptane (4)

51% yield. mp 151-152° C. ¹H NMR (500 MHz, CDCl₃): 8.85 (2H, s), 8.46 (2H, d, J=5.0 Hz,), 8.13 (2H, d, J=7.5 Hz), 7.95 (2H, d, J=5.0 Hz), 7.55-7.57 (2H, m), 7.41 (2H, d, J=8.0 Hz), 7.27-7.28 (2H, m), 4.32 (4H, t, J=7.5 Hz), 1.81-1.88 (4H, m), 1.28-1.37 (6H, m); ¹³C NMR (100 MHz, CDCl₃): δ 141.0, 138.7, 136.3, 131.9, 128.2, 121.8, 120.9, 119.4, 114.4, 109.3, 43.1, 29.0, 28.9, 26.9; ESI-MS m/z: 433.3 (M⁺).

1,8-bis(β-carboline-9-yl) octane (5)

44% yield. mp 180-181° C. ¹H NMR (500 MHz, CDCl₃): δ 8.87 (2H, s), 8.45 (2H, d, J=5.0 Hz), 8.13 (2H, d, J=8.0 Hz), 7.94 (2H, d, J=5.0 Hz), 7.55-7.59 (2H, m), 7.43 (2H, d, J=8.5 Hz), 7.26-7.28 (2H, m), 4.32 (4H, t, J=7.0 Hz), 1.81-1.87 (4H, m), 1.24-1.32 (8H, m); ¹³C NMR (100 MHz, CDCl₃): δ 141.0, 138.7, 136.4, 131.9, 128.1 (4C), 121.7, 120.9, 119.4, 114.4, 109.3, 43.1, 29.0, 28.9, 26.9; ESI-MS m/z: 447.1 (M⁺).

Example 2

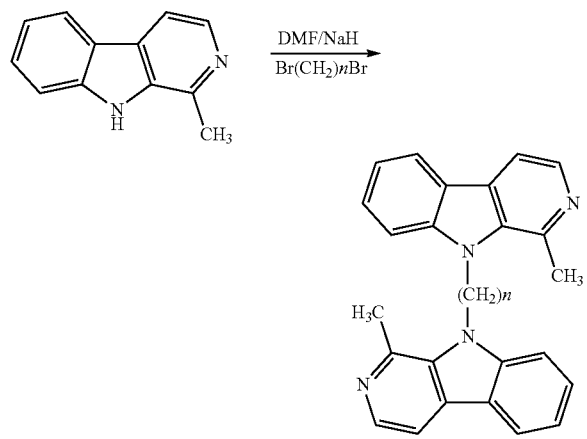

6 n = 3
7 n = 4
8 n = 5
9 n = 6
10 n = 7
11 n = 8
12 n = 9
13 n = 10

Synthesis Process of the bis-β-carboline Compounds (6-13)

1-methyl-β-carboline (2 mmol), 60% NaH (5 mmol), DMF (30 ml) and dihalogenated alkane (1 mmol) were mixed, the reaction mixture was stirred at 60° C. for 8-20 h, TLC detection (eluent:methanol) until the reaction completed. The reaction mixture was poured into 100 ml water and extracted with CH₂Cl₂. The extract liquor was merged extract liquor, washed with water and saturated brine, then dried with anhydrous NaSO₄, the solvent was removed under reduced pressure to give crude product, which was purified vis silica gel column chromatography (CH₂Cl₂/CH₃OH (v/v)=50:1). The eluent containing target product was collected, concentrated under reduced pressure to give the title compound (white solid).

1,3-bis (1-methyl-β-carboline-9-yl) propane (6)

46% yield. mp 239-240° C. ¹H NMR (500 MHz, CDCl₃): δ 8.31 (2H, d, J=5.0 Hz), 8.09 (2H, d, J=8.0 Hz), 7.81 (2H, d, J=5.0 Hz,), 7.49-7.51 (2H, m), 7.24-7.27 (2H, m), 7.20 (2H, d, J=8.0 Hz), 4.54 (4H, t, J=7.5 Hz), 2.74 (6H, s), 2.31-2.37 (2H, m); ¹³C NMR (100 MHz, CDCl₃): δ 141.0, 140.8, 138.4, 134.8, 129.1, 128.3, 121.6, 121.4, 119.9, 112.9, 109.1, 41.9, 31.3, 23.1; EST-MS m/z: 404.9 (M).

1,4-bis(1-methyl-β-carboline-9-yl) butane (7)

62% yield, mp 232-233° C.; IR (KBr) 3432, 3053, 2986, 2933, 2857, 1619, 1561, 1446, 1407, 1362, 1232, 824, 750, 731; ¹H-NMR (500 MHz, DMSO-d6) δ 8.19-8.21 (4H, m), 7.96 (2H, d, J=5.0 Hz), 7.67 (2H, d, J=8.5 Hz), 7.52-7.56 (2H, m), 7.22-7.25 (2H, m), 4.66 (4H, t, J=7.5 Hz), 2.91 (6H, s), 1.84-1.89 (4H, m). ¹³C NMR (100 MHz, CDCl₃): δ 141.4, 141.0, 138.3, 135.0, 129.3, 128.3, 121.6, 121.4, 119.8, 113.0, 109.5, 44.4, 28.1, 23.5. ESI-MS m/z: 419.3 (M⁺).

1,5-bis(1-methyl-β-carboline-9-yl)pentane (8)

40% yield. mp 213-214° C. ¹H NMR (500 MHz, CDCl₃): δ 8.33 (2H, d, J=5.0 Hz), 8.11 (2H, d, J=8.0 Hz), 7.83 (2H, d, J=5.0 Hz), 7.53-7.55 (2H, m), 7.36 (2H, d, J=8.0 Hz), 7.27 (2H, d, J=8.0 Hz), 4.48 (4H, t, J=7.5 Hz), 2.99 (6H, s), 1.83-1.89 (4H, m), 1.44-1.49 (2H, m); ¹³C NMR (100 MHz, CDCl₃): δ 141.3, 141.0, 138.1, 134.9, 129.0, 128.1, 121.4, 121.2, 119.6, 112.8, 109.5, 44.4, 30.6, 24.3, 23.5; ESI-MS m/z: 433.3 (M⁺).

1,6-bis(1-methyl-β-carboline-9-yl) hexane (9)

58% yield, mp 220-221° C.; IR (KBr) 3432, 3053, 2986, 2933, 2857, 1619, 1561, 1446, 1407, 1362, 1232, 824, 750, 731; ¹H-NMR (500 MHz, DMSO-d6) δ 8.19 (4H, d, J=4.5 Hz), 7.95 (2H, d, J=5.0 Hz), 7.64 (2H, d, J=8.5 Hz) m, 7.54-7.57 (2H, m), 7.22-7.25 (2H, m), 4.54 (4H, t, J=8.0 Hz), 2.93 (6H, s), 1.69-1.74 (4H, m), 1.36-1.43 (4H, m). ¹³C NMR (100 MHz, CDCl₃): δ 141.6, 141.0, 137.8, 135.0, 129.2, 128.2, 121.6, 121.3, 119.7, 113.0, 109.6, 44.6, 30.8, 26.8, 23.4. ESI-MS m/z: 447.4 (M⁺).

1,7-bis(1-methyl-β-carboline-9-yl) heptane (10)

26% yield. mp 189-190° C. ¹H NMR (500 MHz, CDCl₃): δ 8.31 (2H, d, J=5.5 Hz), 8.10 (2H, d, J=7.5 Hz), 7.83 (2H, d, J=5.5 Hz), 7.53-7.55 (2H, m), 7.41 (2H, d, J=8.0 Hz), 7.27 (2H, t, J=8.0 Hz), 4.48 (4H, t, J=8.0 Hz), 3.02 (6H, s), 1.77-1.84 (4H, m), 1.36-1.42 (6H, m); ¹³C NMR (100 MHz, CDCl₃): δ 141.4, 141.1, 138.0, 135.0, 129.0, 128.0, 121.4, 121.3, 119.5, 112.9, 109.5, 44.7, 30.6, 29.1, 26.7, 23.5; ESI-MS m/z: 460.9 (M⁺).

1,8-bis(1-methyl-β-carboline-9-yl) octane (11)

41% yield, mp 141-142° C.; IR (KBr) 3425, 3052, 2987, 2928, 2854, 1620, 1562, 1447, 1406, 1359, 1227, 1134, 822, 750, 730; $^{1}$H-NMR (500 MHz, DMSO-d$_6$) δ 8.19 (2H, d, J=5.0 Hz), 8.17 (2H, d, J=8.0 Hz), 7.93-7.94 (2H, d, J=5.0 Hz), 7.63 (2H, d, J=8.0 Hz), 7.54-7.57 (2H, m), 7.21-7.24 (2H, m), 4.52 (4H, t, J=7.5 Hz), 2.94 (6H, s), 1.65-1.69 (4H, m), 1.22-1.31 (8H, m); $^{13}$C NMR (100 MHz, CDCl$_3$): δ 141.3, 141.0, 137.7, 134.9, 128.8, 127.9, 121.3, 121.1, 119.4, 112.7, 109.5, 44.6, 30.5, 29.0, 26.6, 23.3. ESI-MS m/z: 475.4 (M$^+$).

1,9-bis(1-methyl-β-carboline-9-yl) nonane (12)

53% yield. mp 155-156° C. $^{1}$H NMR (500 MHz, CDCl$_3$): δ 8.32 (2H, d, J=5.0 Hz), 8.11 (2H, d, J=7.5 Hz), 7.83 (2H, d, J=5.0 Hz), 7.54-7.57 (2H, m), 7.44 (2H, d, J=8.5 Hz), 7.26-7.28 (2H, m), 4.51 (4H, t, J=7.5 Hz), 3.04 (6H, s), 1.78-1.85 (4H, m), 1.25-1.40 (10H, m); $^{13}$C NMR (100 MHz, CDCl$_3$): δ 141.4, 141.1, 137.9, 135.0, 128.9, 127.9, 121.4, 121.2, 119.5, 112.8, 109.6, 44.8, 30.7, 29.1, 26.8, 23.5; ESI-MS m/z: 488.9 (M).

1,10-bis(1-methyl-β-carboline-9-yl) decane (13)

56% yield, mp 152-154° C.; IR (KBr) 3424, 3049, 2985, 2927, 2849, 1619, 1562, 1445, 1406, 1360, 1330, 1216, 972, 825, 730; $^{1}$H-NMR (500 MHz, DMSO-d$_6$) δ 8.18-8.20 (4H, m), 7.94 (2H, d, J=4.5 Hz), 7.66 (2H, d, J=8.5 Hz), 7.55-7.58 (2H, m), 7.21-7.24 (2H, m), 4.56 (4H, t, J=7.5 Hz), 2.96 (6H, s), 1.68-1.73 (4H, m), 1.15-1.32 (12H, m), $^{13}$C NMR (100 MHz, CDCl$_3$): δ 141.5, 141.2, 137.9, 135.1, 129.0, 128.0, 121.4, 121.3, 119.5, 112.9, 109.7, 44.8, 30.8, 29.3, 29.2, 26.8, 23.5. ESI-MS m/z: 503.4 (M$^+$).

Example 3

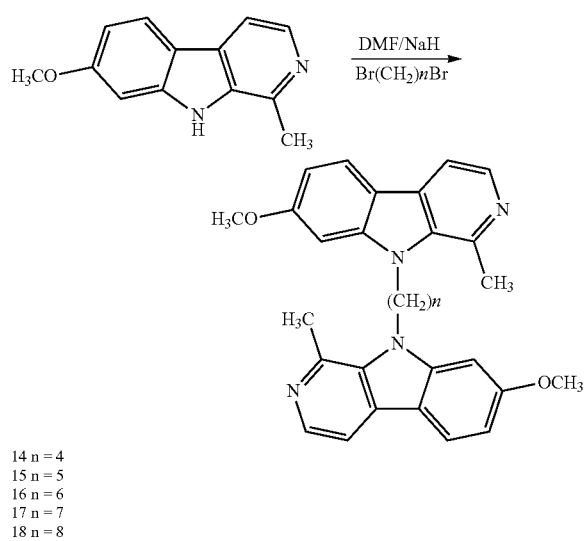

14 n = 4
15 n = 5
16 n = 6
17 n = 7
18 n = 8

Synthesis Process of the bis-β-carboline Compounds (14-18)

Harmine (2 mmol), 60% NaH (5 mmol), DMF (30 ml) and dibromo alkane (1 mmol) were mixed, the reaction mixture was stirred at 60° C. for 8-20 h, TLC detection (eluent:methanol) until the reaction completed. The reaction mixture was poured into 100 ml water and extracted with CH$_2$Cl$_2$. The extract liquor was merged extract liquor, washed with water and saturated brine, then dried with anhydrous NaSO$_4$, the solvent was removed under reduced pressure to give crude product, which was purified vis silica gel column chromatography (CH$_2$Cl$_2$/CH$_3$OH (v/v)=50:1). The eluent containing target product was collected, concentrated under reduced pressure to give the title compound (light yellow solid)

1,4-bis(7-methoxy-1-methyl-β-carboline-9-yl) butane (14)

49% yield. $^{1}$H NMR (300 MHz, CDCl$_3$): δ 8.27 (2H, d, J=5.1 Hz), 7.93 (2H, d, J=8.4 Hz), 7.70 (2H, d, J=5.1 Hz,), 6.86 (2H, dd, J=8.4, 2.1 Hz), 6.70 (2H, d, J=2.1 Hz), 4.48 (4H, t, J=7.2 Hz), 3.87 (6H, s), 2.93 (6H, s), 1.90-1.92 (4H, m); $^{13}$C NMR (100 MHz, CDCl$_3$): δ 160.9, 142.9, 140.3, 138.6, 135.2, 129.6, 122.5, 115.3, 112.3, 108.7, 93.4, 55.7, 44.3, 27.7, 23.4. ESI-MS m/z: 479.6 (M).

1,5-bis(7-methoxy-1-methyl-β-carboline-9-yl)pentane (15)

52% yield. mp 180-181° C. $^{1}$H NMR (500 MHz, CDCl$_3$): δ 8.29 (2H, d, J=5.5 Hz), 7.97 (2H, d, J=8.5 Hz), 7.73 (2H, d, J=5.5 Hz,), 6.88 (2H, dd, J=8.5, 2.0 Hz), 6.77 (2H, d, J=2.0 Hz), 4.43 (4H, t, J=7.5 Hz), 3.88 (6H, s), 2.96 (6H, s), 1.83-1.89 (4H, m), 1.43-1.49 (4H, m); $^{13}$C NMR (100 MHz, CDCl$_3$): δ 160.8, 142.9, 140.3, 138.3, 135.1, 129.4, 122.3, 115.1, 112.2, 108.5, 93.4, 55.6, 44.4, 30.5, 24.3, 23.4; ESI-MS m/z: 492.9 (M$^+$).

1,6-bis(7-methoxy-1-methyl-β-carboline-9-yl) hexane (16)

45% yield. $^{1}$H NMR (500 MHz, CDCl$_3$): δ 8.28 (2H, d, J=5.0 Hz), 7.96 (2H, d, J=8.5 Hz), 7.72 (2H, d, J=5.5 Hz), 6.88 (2H, dd, J=8.5, 2.0 Hz), 6.81 (2H, d, J=2.0 Hz), 4.43 (4H, t, J=7.5 Hz), 3.92 (6H, s), 2.98 (6H, s), 1.79-1.82 (4H, m), 1.41-1.44 (4H, m); $^{13}$C NMR (100 MHz, CDCl$_3$): δ 160.8, 143.0, 140.4, 138.2, 135.2, 129.4, 122.4, 115.2, 112.2, 108.4, 93.5, 55.6, 44.6, 30.6, 26.8, 23.3; ESI-MS m/z: 507.1 (M$^+$).

1,7-bis(7-methoxy-1-methyl-β-carboline-9-yl) heptane (17)

53% yield. mp 199-200° C. $^{1}$H NMR (500 MHz, CDCl$_3$): δ 8.28 (2H, d, J==5.0 Hz), 7.96 (2H, d, J=8.5 Hz), 7.72 (2H, d, J=5.5 Hz), 6.87 (2H, dd, J=8.5, 2.0 Hz), 6.81 (2H, d, J=2.0 Hz), 4.41 (4H, t, J=7.5 Hz), 3.91 (6H, s), 2.98 (6H, s), 1.78-1.81 (4H, m), 1.36-1.44 (6H, m); $^{13}$C NMR (100 MHz, CDCl$_3$): δ 160.7, 142.9, 140.4, 138.3, 135.2, 129.3, 122.3, 115.2, 112.2, 108.4, 93.4, 55.6, 44.7, 30.5, 29.2, 26.8, 23.4; ESI-MS m/z: 520.9 (M$^+$).

1,8-bis(7-methoxy-1-methyl-β-carboline-9-yl) nonane (18)

71% yield. mp 181-182° C. $^{1}$H NMR (500 MHz, CDCl$_3$): δ 8.27 (2H, d, J=5.0 Hz), 7.97 (2H, d, J=8.5 Hz), 7.76 (2H, d, J=5.0 Hz), 6.89 (2H, dd, J=8.5, 2.0 Hz), 6.83 (2H, d, J=2.0 Hz), 4.44 (4H, t, J=7.5 Hz), 3.93 (6H, s), 3.04 (6H, s), 1.76-1.82 (4H, m), 1.31-1.39 (8H, m); $^{13}$C NMR (100 MHz, CDCl$_3$): δ 160.8, 143.1, 140.3, 137.9, 135.2, 129.4, 122.3, 115.2, 112.2, 108.5, 93.5, 55.6, 44.8, 30.4, 29.2, 26.8, 23.2; ESI-MS m/z: 535.0 (M$^+$).

Example 4

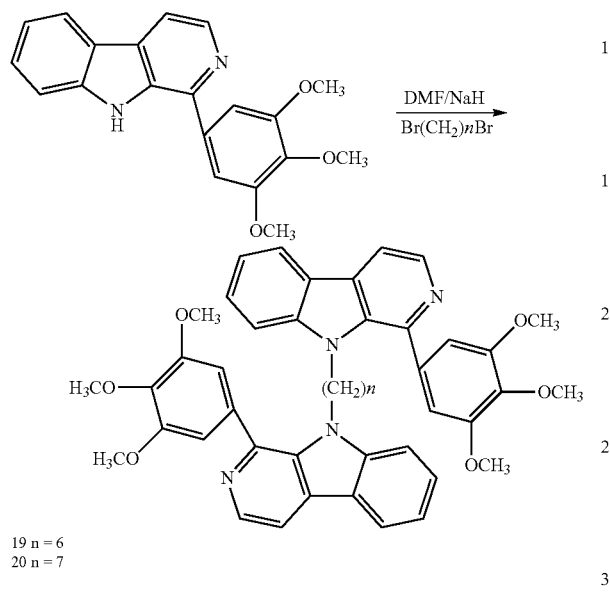

19 n = 6
20 n = 7

Synthesis Process of the bis-β-carboline Compounds (19-20)

(3,4,5-trimethoxy phenyl)-β-carboline (2 mmol), 60% NaH (5 mmol), DMF (30 ml) and dihalogenated alkane (1 mmol) were mixed, the reaction mixture was stirred at 60° C. for 8-20 h, TLC detection (eluent:methanol) until the reaction completed. The reaction mixture was poured into 100 ml water and extracted with CH$_2$Cl$_2$. The extract liquor was merged extract liquor, washed with water and saturated brine, then dried with anhydrous NaSO$_4$, the solvent was removed under reduced pressure to give crude product, which was purified vis silica gel column chromatography (CH$_2$Cl$_2$/CH$_3$OH (v/v)=50:1). The eluent containing target product was collected, concentrated under reduced pressure to give the title compound.

1,6-bis[1-(3,4,5-trimethoxy)phenyl-β-carboline-9-yl) hexane (19)

to give white solid 0.57 g. 76% yield. mp 199-200° C. $^1$H NMR (500 MHz, CDCl$_3$): δ 8.47 (2H, d, J=5.5 Hz), 8.16 (2H, d, J=8.0 Hz), 7.96 (2H, d, J=5.5 Hz), 7.55-7.59 (2H, m), 7.36 (2H, d, J=8.5 Hz), 7.28-7.31 (2H, m), 6.73 (4H, s), 3.88 (4H, t, J=7.5 Hz), 3.84 (6H, s), 3.74 (12H, s), 1.22-1.32 (4H, m), 0.67-0.70 (4H, m); $^{13}$C NMR (100 MHz, CDCl$_3$): 152.9, 143.8, 141.8, 138.1, 138.0, 135.4, 133.7, 130.2, 128.4, 121.5, 121.2, 119.8, 113.6, 110.0, 106.4, 60.8, 56.0, 44.2, 28.9, 26.1; ESI-MS m/z: 750.6 (M$^+$).

1,7-bis[1-(3,4,5-trimethoxy)phenyl-β-carboline-9-yl) heptane (20)

to give light yellow oil 0.56 g. 62% yield. $^1$H NMR (500 MHz, CDCl$_3$): δ 8.46 (2H, d, J=5.1 Hz), 8.14 (2H, d, J=7.8 Hz), 7.95 (2H, d, J=5.1 Hz), 7.54-7.59 (2H, m), 7.39 (2H, d, J=7.8 Hz), 7.25-7.29 (2H, m), 6.75 (4H, s), 3.91 (4H, t, J=7.8 Hz), 3.83 (6H, s), 3.80 (12H, s), 1.25-1.38 (4H, m), 0.72-0.86 (6H, m); $^{13}$C NMR (100 MHz, CDCl$_3$): β 153.1, 144.0, 142.1, 138.3, 135.7, 134.0, 130.4, 128.6, 121.8, 121.5, 120.1, 114.0, 110.4, 106.7, 61.2, 56.4, 44.7, 29.5, 29.1, 26.8; ESI-MS m/z: 765.4 (M$^+$).

Example 5

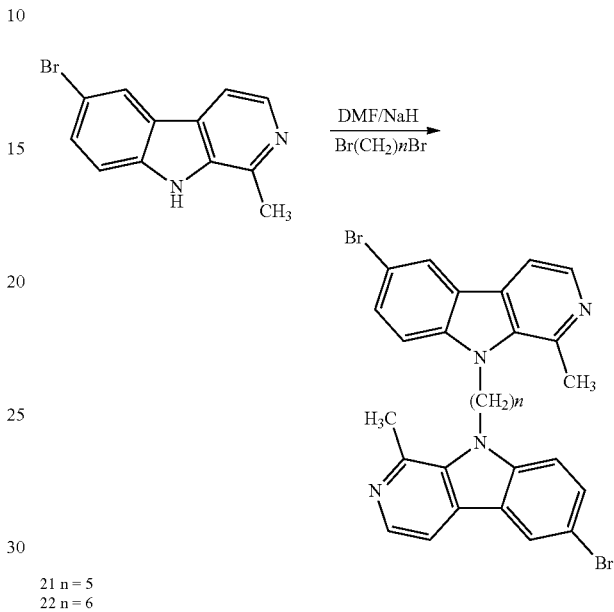

21 n = 5
22 n = 6

Synthesis Process of the bis-β-carboline Compounds (21-22)

6-bromo-1-methyl-β-carboline (0.52 g, 2 mmol), 60% NaH (5 mmol), DMF (30 ml) and dihalogenated alkane (1 mmol) were mixed, the reaction mixture was stirred at 60° C. for 8-20 h, TLC detection (eluent:methanol) until the reaction completed. The reaction mixture was poured into 100 ml water and extracted with CH$_2$Cl$_2$. The extract liquor was merged extract liquor, washed with water and saturated brine, then dried with anhydrous NaSO$_4$, the solvent was removed under reduced pressure to give crude product, which was purified vis silica gel column chromatography (CH$_2$Cl$_2$/CH$_3$OH (v/v)=50:1). The eluent containing target product was collected, concentrated under reduced pressure to give the title compound.

1,5-bis(6-bromo-1-methyl-β-carboline-9-yl) hexane (21)

to give white solid 0.21 g, 35% yield. mp 208-209° C. $^1$H NMR (300 MHz, CDCl$_3$): δ 8.33 (2H, d, J=5.4 Hz), 8.20 (2H, d, J=1.8 Hz), 7.76 (2H, d, J=5.4 Hz), 7.58 (2H, dd, J=1.8 Hz, 8.7 Hz), 7.18 (2H, d, J=8.7 Hz), 4.45 (4H, t, J=7.5 Hz), 2.98 (6H, s), 1.78-1.88 (4H, m), 1.32-1.42 (2H, m); $^{13}$C NMR (75 MHz, CDCl$_3$): δ 141.5, 140.0, 138.6, 135.3, 131.0, 128.1, 124.4, 123.0, 113.1, 112.6, 111.3, 44.9, 31.1, 24.8, 24.0; ESI-MS m/z: 605.5 (M$^4$).

1,6-bis(6-bromo-1-methyl-β-carboline-9-yl) hexane (22)

to give white solid 0.41 g, 67% yield. mp 275-276° C. $^1$H NMR (500 MHz, CDCl$_3$): δ 8.33 (2H, d, J=5.0 Hz), 8.22

(21-1, d, J=2.0 Hz), 7.77 (2H, d, J=5.0 Hz), 7.62 (2H, dd, J=8.5, 2.0 Hz), 7.24 (2H, d, J=8.5 Hz), 4.47 (4H, t, J=7.5 Hz), 2.99 (6H, s), 1.76-1.83 (4H, m), 1.35-1.41 (4H, m); $^{13}$C NMR (125 MHz, CDCl$_3$): δ 141.5, 140.0, 138.5, 135.3, 130.8, 128.0, 124.2, 123.0, 113.0, 112.4, 111.1, 44.8, 30.7, 26.8, 23.5; ESI-MS m/z: 604.0 (M$^+$).

Example 6

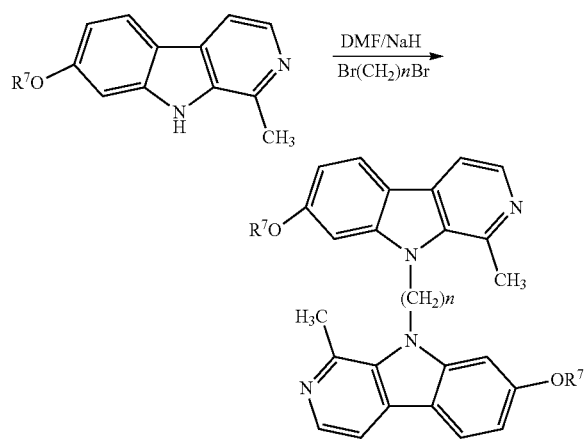

| 23 R$^7$ = C$_4$H$_9$ | n = 4 |
| 24 R$^7$ = C$_4$H$_9$ | n = 6 |
| 25 R$^7$ = CH(CH$_3$)$_2$ | n = 6 |
| 26 R$^7$ = CH(CH$_3$)$_2$ | n = 9 |

Synthesis Process of the bis-β-carboline Compounds (23-26)

7-alkoxy-1-methyl-β-carboline (2 mmol), 60 NaH (5 mmol), DMF (30 ml) and dihalogenated alkane (1 mmol) were mixed, the reaction mixture was stirred at 60° C. for 8-20 h, TLC detection (eluent:methanol) until the reaction completed. The reaction mixture was poured into 100 ml water and extracted with CH$_2$Cl$_2$. The extract liquor was merged extract liquor, washed with water and saturated brine, then dried with anhydrous NaSO$_4$, the solvent was removed under reduced pressure to give crude product, which was purified vis silica gel column chromatography (CH$_2$Cl$_2$/CH$_3$OH (v/v)=50:1). The eluent containing target product was collected, concentrated under reduced pressure to give the title compound.

1,4-bis(7-n-butoxy-1-methyl-β-carboline-9-yl) butane (23)

to give white solid 0.22 g, 62% yield. mp 193-194° C. $^1$H NMR (300 MHz, CDCl$_3$): δ 8.26 (2H, d, J=5.1 Hz), 7.92 (2H, d, J=8.4 Hz), 7.68 (2H, d, J=5.1 Hz), 6.85 (2H, dd, J=1.8 Hz, 8.4 Hz), 6.71 (2H, d, J=1.8 Hz), 4.41 (4H, t, J=6.9 Hz), 4.01 (4H, t, J=6.6 Hz), 2.91 (6H, s), 1.79-1.89 (8H, m), 1.48-1.61 (4H, m), 1.02 (6H, t, J=7.5 Hz); $^{13}$C NMR (100 MHz, CDCl$_3$): δ 160.6, 143.1, 140.3, 138.6, 135.3, 129.8, 122.6, 115.3, 112.5, 109.4, 94.3, 68.5, 44.6, 31.8, 28.2, 23.7, 19.7, 14.3; ESI-MS m/z: 563.4 (M).

1,6-bis(7-n-butoxy-1-methyl-β-carboline-9-yl) hexane (24)

to give white solid 0.23 g, 65% yield. $^1$H NMR (500 MHz, CDCl$_3$): δ 8.27 (2H, d, J=5.0 Hz), 7.95 (2H, d, J=8.5 Hz), 7.71 (2H, d, J=5.0 Hz), 6.87 (2H, dd, J=8.5, 2.0 Hz), 6.81 (2H, d, J=2.0 Hz), 4.42 (4H, t, J=7.5 Hz), 4.06 (4H, t, J=7.0 Hz), 2.97 (6H, s), 1.79-1.83 (8H, m), 1.49-1.57 (4H, m), 1.41-1.44 (4H, m), 0.99 (6H, t, J=6.0 Hz); $^{13}$C NMR (100 MHz, CDCl$_3$): δ 160.3, 143.0, 140.3, 138.2, 135.2, 129.4, 122.2, 115.1, 121.1, 108.8, 94.2, 68.1, 44.6, 31.3, 30.6, 26.8, 23.3, 19.2, 13.8; ESI-MS m/z: 590.4 (M$^+$).

1,6-bis(7-isopropoxy-1-methyl-β-carboline-9-yl) hexane (25)

to give white solid 0.25 g, 71% yield. mp 155-156° C. $^1$H NMR (300 MHz, CDCl$_3$): δ 8.25 (2H, d, J=5.4 Hz), 7.95 (2H, d, J=8.7 Hz), 7.71 (2H, d, J=5.4 Hz), 6.86 (2H, dd, J=1.8 Hz, 8.7 Hz), 6.82 (2H, d, J=1.8 Hz), 4.62-4.74 (2H, m), 4.41 (4H, t, J=7.5 Hz), 2.98 (6H, s), 1.75-1.85 (4H, m), 1.39-1.41 (16H, m); $^{13}$C NMR (100 MHz, CDCl$_3$): δ 159.2, 143.3, 140.5, 138.3, 135.4, 129.7, 122.6, 115.4, 112.5, 110.1, 96.4, 70.9, 45.0, 31.0, 27.3, 23.7, 22.6; ESI-MS m/z: 562.5 (M$^+$).

1,9-bis(7-isopropoxy-1-methyl-β-carboline-9-yl) nonane (26)

to give white solid 0.4 g, 67% yield. mp 161-162° C. $^1$H NMR (300 MHz, CDCl$_3$): δ 8.25 (2H, d, J=5.1 Hz), 7.94 (2H, d, J=9.3 Hz), 7.70 (2H, d, J=5.1 Hz), 6.84-6.87 (4H, m), 4.63-4.75 (2H, m), 4.41 (4H, t, J=7.8 Hz), 3.00 (6H, s), 1.75-1.85 (4H, m), 1.26-1.45 (22H, m); $^{13}$C NMR (100 MHz, CDCl$_3$): δ 159.1, 143.2, 140.6, 138.4, 135.5, 129.5, 122.5, 115.4, 112.4, 110.0, 96.3, 70.8, 45.1, 31.0, 29.8, 29.6, 27.3, 23.8, 22.5; ESI-MS m/z: 605.5 (M$^+$).

Example 7

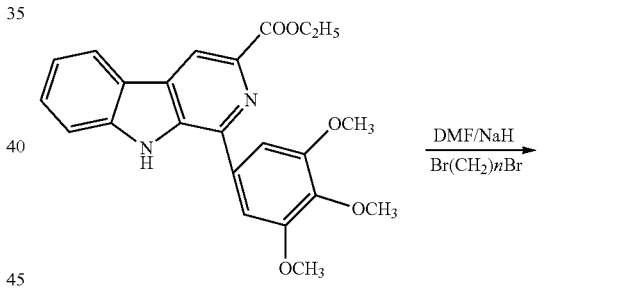

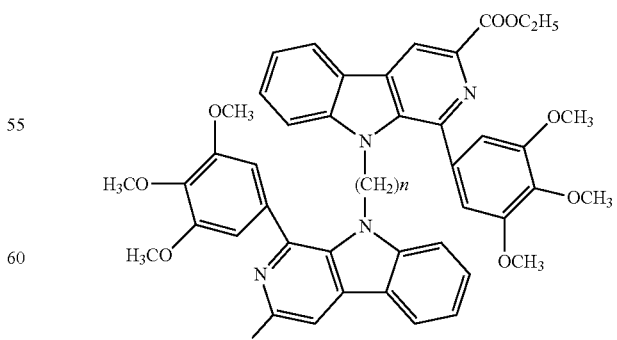

27 n = 6
28 n = 9

Synthesis Process of the bis-β-carboline Compounds (27-28)

A solution of ethyl 1-(3,4,5-trimethoxy)phenyl-β-carboline-3-carboxylate (0.81 g, 2 mmol) and 60% NaH (5 mmol) in DMF (30 ml) was stirred at room temperature in 100 ml round-bottomed flask. After 5 min, the dihalogenated alkane (1 mmol) was added and the reaction mixture was stirred at 60° C. for 8-20 h, TLC detection (eluent:methanol) until the reaction completed. The reaction mixture was poured into 100 ml water and extracted with $CH_2Cl_2$. The extract liquor was merged extract liquor, washed with water and saturated brine, then dried with anhydrous $NaSO_4$, the solvent was removed under reduced pressure to give crude product, which was purified vis silica gel column chromatography ($CH_2Cl_2/CH_3COOC_2H_5$ (v/v)=1:1, $CH_3COOC_2H_5/CH_3OH$ (v/v)=20:1).

The eluent containing target product was collected, concentrated under reduced pressure to give the title compound.

1,6-bis[1-(3,4.5-trimethoxy)phenyl-β-carboline-β-ethyoxylcarbonyl-9-yl]hexane (27)

to give white solid 0.6 g, 67% yield, mp 264-265° C. $^1$H NMR (300 MHz, $CDCl_3$): δ 8.83 (2H, s), 8.21 (2H, d, J=7.8 Hz), 7.58-7.64 (2H, m), 7.33-7.40 (4H, m), 6.73 (4H, s), 4.50 (4H, q, J=7.2 Hz), 3.83-3.89 (10H, m), 3.73 (12H, s), 1.23-1.28 (4H, m), 1.46 (6H, t, J=7.2 Hz), 0.65-0.73 (4H, m); $^{13}$C NMR (75 MHz, $CDCl_3$): δ 166.1, 153.2, 143.8, 142.4, 138.6, 137.1, 135.5, 134.9, 130.3, 129.1, 122.0, 121.7, 121.0, 116.9, 110.7, 107.2, 61.8, 61.1, 56.4, 44.7, 29.6, 26.6, 14.9; ESI-MS m/z: 895.5 (M$^+$).

1,9-bis[1-(3,4.5-trimethoxy)phenyl-β-carboline-3-ethyoxylcarbonyl-9-yl]nonane (28)

to give yellow oil 0.25 g, 53 yield. $^1$H NMR (300 MHz, $CDCl_3$): δ 8.85 (2H, s), 8.23 (2H, d, J=7.8 Hz), 7.58-7.63 (2H, m), 7.32-7.47 (4H, m), 6.82 (2H, s), 6.79 (2H, s), 4.51 (4H, q, J=7.2 Hz), 3.84-4.00 (22H, m), 1.37-1.58 (10H, m), 1.24-1.28 (4H, m), 0.84-0.97 (6H, m); $^{13}$C NMR (75 MHz, $CDCl_3$): δ 166.1, 153.2, 143.8, 142.4, 138.6, 136.9, 135.6, 135.0, 130.3, 129.0, 121.9, 121.8, 120.9, 116.9, 110.7, 107.0, 61.7, 61.2, 56.5, 45.0, 29.8, 29.6, 29.4, 27.0, 14.9; ESI-MS m/z: 937.5 (M$^+$).

Example 8

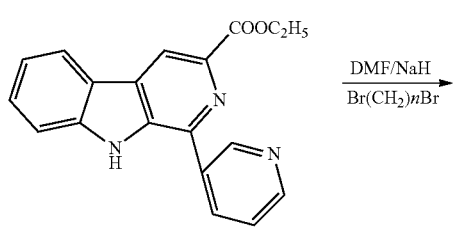

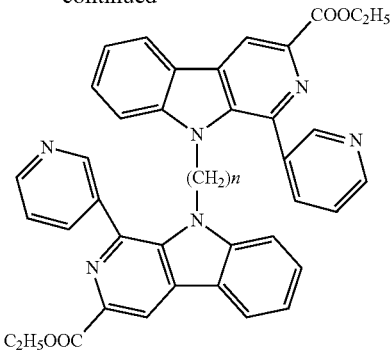

29 n = 5
30 n = 6

Synthesis Process of the bis-β-carboline Compounds (29-30)

A solution of ethyl 1-(pyridyl-3-yl)-β-carboline-3-carboxylate (0.63 g, 2 mmol) and 60% NaH (5 mmol) in DMF (30 ml) was stirred at room temperature in 100 ml round-bottomed flask. After 5 min, the dihalogenated alkane (1 mmol) was added and the reaction mixture was stirred at 60° C. for 8-20 h, TLC detection (eluent:methanol) until the reaction completed. The reaction mixture was poured into 100 ml water and extracted with $CH_2Cl_2$. The extract liquor was merged extract liquor, washed with water and saturated brine, then dried with anhydrous $NaSO_4$, the solvent was removed under reduced pressure to give crude product, which was purified vis silica gel column chromatography ($CH_2Cl_2/CH_3COOC_2H_5$ (v/v)=1:1, $CH_3COOC_2H_5/CH_3OH$ (v/v)=20:1).

The eluent containing target product was collected, concentrated under reduced pressure to give the title compound.

1,5-bis[3-ethyoxylcarbonyl-1-(pyridine-3-yl)-β-carboline-9-yl]pentane (29)

to give yellow solid 0.3 g, 43% yield. mp 172-174° C. $^1$H NMR (300 MHz, $CDCl_3$): δ 8.90 (2H, s), 8.76 (2H, d, J=2.1 Hz), 8.46-8.48 (2H, dd, J=1.5, 5.1 Hz), 8.26 (2H, d, J=8.1 Hz), 7.83-7.87 (2H, m), 7.61-7.66 (2H, m), 7.33-7.43 (4H, m), 7.21-7.26 (2H, m), 4.53 (4H, q, J=6.9 Hz), 3.81 (4H, t, J=7.8 Hz), 1.49 (6H, t, J=6.9 Hz), 1.01-1.11 (4H, m), 0.31-0.39 (2H, m); $^{13}$C NMR (75 MHz, $CDCl_3$): δ 165.9, 150.3, 149.9, 142.4, 140.3, 137.9, 137.1, 135.8, 135.5, 131.0, 129.4, 123.2, 122.1, 121.7, 121.4, 117.3, 110.6, 62.0, 44.5, 28.6, 23.5, 14.8; ESI-MS m/z: 703.5 (M$^+$).

1,6-bis[3-ethyoxylcarbonyl-1-(pyridine-3-yl)-β-carboline-9-yl]hexane (30)

to give yellow solid 0.35 g, 49% yield. mp 221-222° C. $^1$H NMR (300 MHz, $CDCl_3$): δ 8.88 (2H, s), 8.83 (2H, d, J=1.5 Hz), 8.67 (2H, dd, J=1.5 Hz, 5.1 Hz), 8.23 (2H, d, J=7.8 Hz), 7.91-7.95 (2H, m), 7.59-7.65 (2H, m), 7.35-7.41 (6H, m), 4.51 (4H, q, J=7.2 Hz), 3.87 (4H, t, J=7.8 Hz), 1.48 (6H, t, J=7.2 Hz), 1.11-1.21 (4H, m), 0.51-0.60 (4H, m); $^{13}$C NMR (75 MHz, $CDCl_3$): δ 165.9, 150.4, 149.9, 142.5, 140.4, 137.8, 137.2, 135.8, 135.6, 131.1, 129.3, 123.3, 122.1, 121.7, 121.3, 117.2, 110.7, 61.9, 44.8, 29.0, 26.2, 14.8; ESI-MS m/z: 717.5 (M$^+$).

Example 9

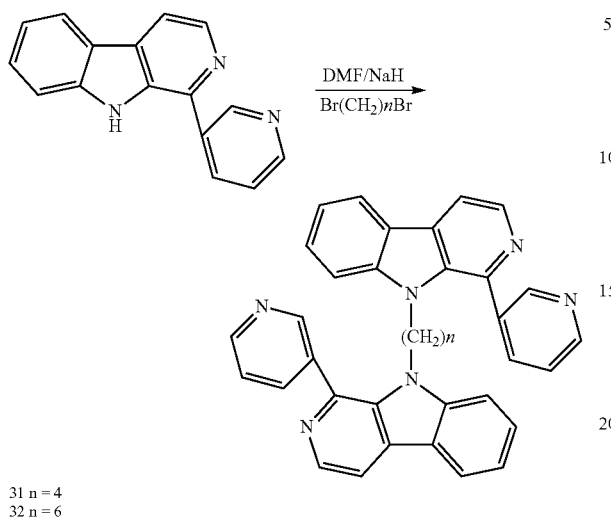

31 n = 4
32 n = 6

Synthesis Process of the bis-β-carboline
Compounds (31-32)

A solution of ethyl 1-(pyridyl-3-yl)-β-carbolinerboxylate (0.49 g, 2 mmol) and 60% NaH (5 mmol) in DMF (30 ml) was stirred at room temperature in 100 ml round-bottomed flask. After 5 min, the dihalogenated alkane (1 mmol) was added and the reaction mixture was stirred at 60° C. for 8-20 h, TLC detection (eluent:methanol) until the reaction completed. The reaction mixture was poured into 100 ml water and extracted with $CH_2Cl_2$. The extract liquor was merged extract liquor, washed with water and saturated brine, then dried with anhydrous $NaSO_4$, the solvent was removed under reduced pressure to give crude product, which was purified vis silica gel column chromatography ($CH_2Cl_2$/$CH_3COOC_2H_5$ (v/v)=1:1, $CH_3COOC_2H_5$/$CH_3OH$ (v/v)=20:1).

The eluent containing target product was collected, concentrated under reduced pressure to give the title compound.

1,4-bis[1-(pyridine-3-yl)-β-carboline-9-yl] butane (31)

to give yellow solid 0.26 g, 46% yield. mp 224-225° C. $^1$H NMR (300 MHz, $CDCl_3$): δ 8.60-8.62 (4H, m), 8.50 (2H, d, J=5.1 Hz), 8.17 (2H, d, J=7.8 Hz), 7.95 (2H, d, J=5.1 Hz), 7.52-7.62 (4H, m), 7.32-7.37 (2H, m), 7.18-7.24 (4H, m), 3.67 (4H, t, J=7.2 Hz), 0.76-0.84 (4H, m); $^{13}$C NMR (75 MHz, $CDCl_3$): δ 150.1, 149.6, 142.2, 140.3, 139.1, 136.6, 135.9, 133.9, 130.9, 129.0, 123.2, 122.0, 121.3, 120.5, 114.4, 110.2, 43.9, 26.1; ESI-MS m/z: 545.5 (M$^+$).

1,6-bis[1-(pyridine-3-yl)-β-carboline-9-yl] hexane (32)

to give yellow solid 0.32 g, 56% yield. $^1$H NMR (300 MHz, $CDCl_3$): δ 8.81-8.82 (2H, m), 8.67 (2H, d, J=3.9 Hz), 8.52 (2H, d, J=5.1 Hz), 8.16 (2H, d, J=7.8 Hz), 7.99 (2H, d, J=5.1 Hz), 7.87-7.91 (2H, m), 7.55-7.60 (2H, m), 7.28-7.39 (6H, m), 3.84 (4H, t, J=7.8 Hz), 1.08-1.18 (4H, m), 0.52-0.57 (4H, m); $^{13}$C NMR (75 MHz, $CDCl_3$): δ 150.1, 149.6, 142.2, 140.5, 138.9, 136.8, 136.1, 134.4, 131.0, 128.9, 123.3, 121.9, 121.4, 120.4, 114.5, 110.4, 44.6, 28.8, 26.3; ESI-MS m/z: 573.5 (M$^+$).

Example 10

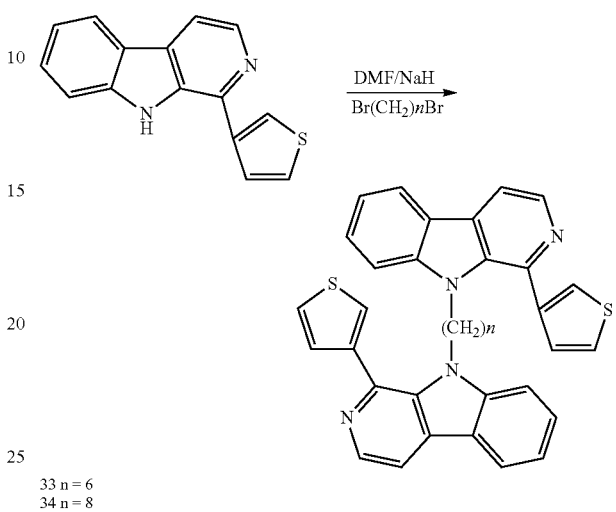

33 n = 6
34 n = 8

Synthesis Process of the bis-β-carboline
Compounds (33-34)

A solution of ethyl 1-(thiophere-3-yl)-β-carbolinerboxylate (0.50 g, 2 mmol) and 60% NaH (5 mmol) in DMF (30 ml) was stirred at room temperature in 100 ml round-bottomed flask. After 5 min, the dihalogenated alkane (1 mmol) was added and the reaction mixture was stirred at 60° C. for 8-20 h, TLC detection (eluent:methanol) until the reaction completed. The reaction mixture was poured into 100 ml water and extracted with $CH_2Cl_2$. The extract liquor was merged extract liquor, washed with water and saturated brine, then dried with anhydrous $NaSO_4$, the solvent was removed under reduced pressure to give crude product, which was purified vis silica gel column chromatography ($CH_2Cl_2$/$CH_3COOC_2H_5$ (v/v)=1:1, $CH_3COOC_2H_5$/$CH_3OH$ (v/v)=20:1).

The eluent containing target product was collected, concentrated under reduced pressure to give the title compound.

1,6-bis[1-(3-thienyl)-β-carboline-9-yl) hexane (33)

to give white solid 0.37 g, 64% yield. mp 198-199° C. $^1$H NMR (300 MHz, $CDCl_3$): δ 8.50 (2H, d, J=5.1 Hz), 8.15 (2H, d, J=7.8 Hz), 7.96 (2H, d, J=5.1 Hz), 7.55-7.60 (2H, m), 7.27-7.43 (6H, m), 7.19-7.21 (2H, m), 7.08-7.10 (2H, m), 4.03 (4H, t, J=7.8 Hz), 1.21-1.30 (4H, m), 0.69-0.74 (4H, m); $^{13}$C NMR (75 MHz, $CDCl_3$): δ 142.3, 141.3, 138.7, 137.3, 134.9, 131.0, 128.8, 128.5, 127.2, 126.9, 121.9, 121.5, 120.3, 114.4, 110.5, 44.5, 29.2, 26.5; ESI-MS m/z: 583.4 (M$^+$).

1,8-bis[1-(3-thienyl)-β-carboline-9-yl) octane (34)

to give yellow solid 0.43 g, 70% yield. mp 161-162° C. $^1$H NMR (300 MHz, $CDCl_3$): δ 8.50 (2H, d, J=5.1 Hz), 8.15 (2H, d, J=7.2 Hz), 7.96 (2H, d, J=5.1 Hz), 7.56-7.61 (2H, m), 7.41-7.44 (4H, m), 7.22-7.32 (4H, m), 7.08-7.11 (2H, m), 4.09 (4H, t, J=7.5 Hz), 1.32-1.42 (4H, m), 0.80-0.88 (8H, m); $^{13}$C NMR (75 MHz, CDCl$_3$): δ 142.4, 141.3, 138.6, 137.3, 135.0, 131.0, 128.8, 128.4, 127.2, 126.8, 121.9, 121.5, 120.2, 114.4, 110.5, 44.7, 29.3, 29.2, 26.9; ESI-MS m/z: 611.4 (M$^+$).

Example 11

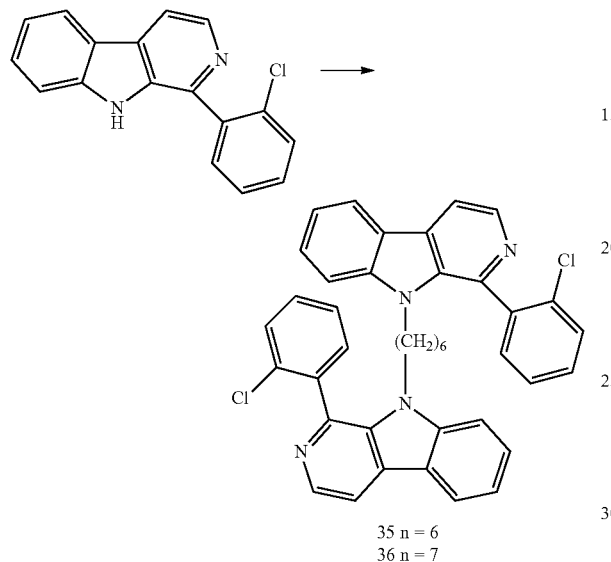

35 n = 6
36 n = 7

Synthesis Process of the bis-β-carboline Compounds (35-36)

A solution of 1-(2-chloro)phenyl-β-carboline (0.56 g, 2 mmol) and 60% NaH (5 mmol) in DMF (30 ml) was stirred at room temperature in 100 ml round-bottomed flask. After 5 min, the dihalogenated alkane (1 mmol) was added and the reaction mixture was stirred at 60° C. for 8-20 h, TLC detection (eluent:methanol) until the reaction completed. The reaction mixture was poured into 100 ml water and extracted with CH$_2$Cl$_2$. The extract liquor was merged extract liquor, washed with water and saturated brine, then dried with anhydrous NaSO$_4$, the solvent was removed under reduced pressure to give crude product, which was purified vis silica gel column chromatography (CH$_2$Cl$_2$/CH$_3$COOC$_2$H$_5$ (v/v)=1:1, CH$_3$COOC$_2$H$_5$/CH$_3$OH (v/v)=20:1).

The eluent containing target product was collected, concentrated under reduced pressure to give the title compound.

1,6-bis[1-(2-chlorophenyl)(i-carboline-9-yl) hexane (35)

to give white solid. 90% yield. mp 210-211° C. $^1$H NMR (300 MHz, CDCl$_3$): δ 8.52 (2H, d, J=5.1 Hz), 8.18 (2H, 7.8 Hz), 8.02 (2H, d, J=5.1 Hz), 7.54-7.59 (2H, m), 7.43-7.49 (4H, m), 7.27-7.39 (8H, m), 3.67-3.89 (4H, m), 1.17-1.39 (4H, m), 0.56-0.69 (4H, m); $^{13}$C NMR (75 MHz, CDCl$_3$): δ 141.8, 141.1, 139.0, 138.5, 134.4, 134.3, 131.7, 130.2, 130.1, 129.6, 128.7, 126.9, 121.9, 121.4, 120.1, 114.5, 110.0, 44.3, 29.4, 26.6; ESI-MS m/z: 639.3 (M$^+$).

1,7-bis[1-(2-chlorophenyl)-β-carboline-9-yl) heptane (36)

to give yellow oil 1.75% yield. $^1$H NMR (300 MHz, CDCl$_3$): 8.53 (2H, d, J=5.1 Hz), 8.18 (2H, d, J=7.8 Hz), 8.02 (2H, d, 7.55-7.60 (2H, m), 7.46-7.52 (4H, m), 7.27-7.39 (8H, m), 3.70-3.93 (4H, m), 1.32-1.42 (4H, m), 0.56-0.85 (6H, m); $^{13}$C NMR (75 MHz, CDCl$_3$): δ 141.9, 141.1, 139.0, 138.3, 134.4, 134.3, 131.7, 130.2, 130.1, 129.6, 128.7, 126.9, 121.9, 121.4, 120.1, 114.6, 110.1, 44.4, 29.4, 28.9, 26.9; ESI-MS m/z: 653.3 (M$^+$).

Example 12

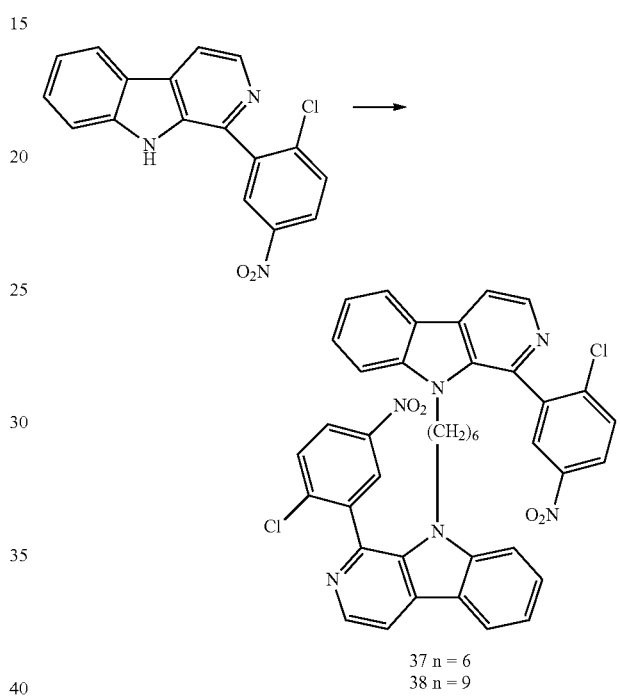

37 n = 6
38 n = 9

Synthesis Process of the bis-β-carboline Compounds (37-38)

A solution of 1-(2-chloro-5-nitro)phenyl-β-carboline (0.64 g, 2 mmol) and 60% NaH (5 mmol) in DMF (30 ml) was stirred at room temperature in 100 ml round-bottomed flask. After 5 min, the dihalogenated alkane (1 mmol) was added and the reaction mixture was stirred at 60° C. for 8-20 h, TLC detection (eluent:methanol) until the reaction completed. The reaction mixture was poured into 100 ml water and extracted with CH$_2$Cl$_2$. The extract liquor was merged extract liquor, washed with water and saturated brine, then dried with anhydrous NaSO$_4$, the solvent was removed under reduced pressure to give crude product, which was purified vis silica gel column chromatography (CH$_2$Cl$_2$/CH$_3$COOC$_2$H$_5$ (v/v)=1:1, CH$_3$COOC$_2$H$_5$/CH$_3$OH (v/v)=20:1).

The eluent containing target product was collected, concentrated under reduced pressure to give the title compound.

1,6-bis[1-(2-chloro-5-nitro-phenyl)-⊕-carboline-9-yl) hexane (37)

55% yield. $^1$H NMR (300 MHz, CDCl$_3$): δ 8.52-8.54 (2H, m), 8.38-8.40 (2H, m), 8.16-8.27 (4H, m), 8.05-8.08 (2H, m), 7.57-7.67 (4H, m), 7.29-7.37 (4H, m), 3.78-3.91 (2H, m), 3.52-3.67 (2H, m), 1.09-1.27 (4H, m), 0.44-0.65 (4H, m); $^{13}$C NMR (75 MHz, CDCl$_3$): δ 146.3, 141.9, 141.5, 140.4, 138.6, 138.3, 134.1, 131.0, 130.7, 129.2, 126.5, 124.7, 122.0, 121.3, 120.5, 115.4, 110.2, 44.3, 29.5, 26.8; ESI-MS m/z: 729.3 (M$^+$).

1,9-bis[1-(2-chloro-5-nitrophenyl)-β-carboline-9-yl) nonane (38)

41% yield. $^1$H NMR (300 MHz, CDCl$_3$): δ 8.52-8.54 (2H, m), 8.46 (2H, d, J=2.7 Hz), 8.26-8.32 (2H, m), 8.19 (2H, d, J=7.8 Hz), 8.07 (2H, dd, J=1.8 Hz, 5.1 Hz), 7.68-7.73 (2H, m), 7.58-7.64 (2H, m), 7.41-7.45 (2H, m), 7.29-7.35 (2H, m), 3.91-4.02 (2H, m), 3.60-3.75 (2H, m), 1.24-1.34 (4H, m), 0.68-0.90 (10H, m); $^{13}$C NMR (75 MHz, CDCl$_3$): δ 146.4, 142.0, 141.5, 140.5, 138.5, 138.4, 134.2, 130.8, 130.7, 129.1, 126.6, 124.8, 121.9, 121.2, 120.4, 115.3, 110.2, 44.6, 29.6, 29.3, 27.1; ESI-MS m/z: 771.3 (M$^+$).

Example 13

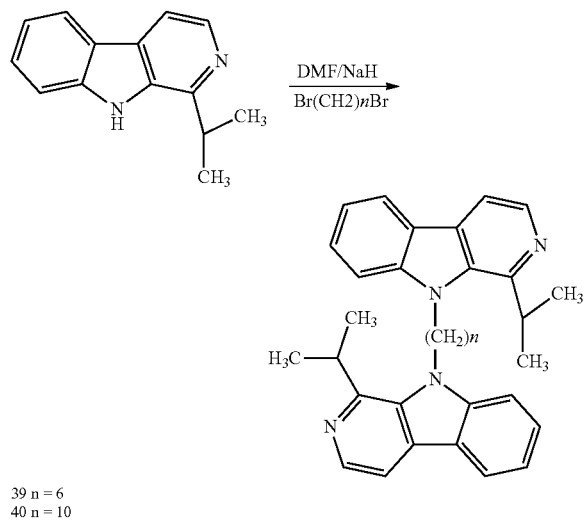

39 n = 6
40 n = 10

Synthesis Process of the bis-β-carboline Compounds (39-40)

A solution of 1-isopropyl-β-carboline (0.42 g, 2 mmol) and 60% NaH (5 mmol) in DMF (30 ml) was stirred at room temperature in 100 ml round-bottomed flask. After 5 min, the dihalogenated alkane (1 mmol) was added and the reaction mixture was stirred at 60° C. for 8-20 h, TLC detection (eluent:methanol) until the reaction completed. The reaction mixture was poured into 100 ml water and extracted with CH$_2$Cl$_2$. The extract liquor was merged extract liquor, washed with water and saturated brine, then dried with anhydrous NaSO$_4$, the solvent was removed under reduced pressure to give crude product, which was purified vis silica gel column chromatography (CH$_2$Cl$_2$/CH$_3$COOC$_2$H$_5$ (v/v)=1:1, CH$_3$COOC$_2$H$_5$/CH$_3$OH (v/v)=20:1).

The eluent containing target product was collected, concentrated under reduced pressure to give the title compound.

1,6-bis(1-isopropyl-β-carboline-9-yl) hexane (39)

to give white solid 0.14 g. 28% yield. mp 241-242° C. $^1$H NMR (300 MHz, CDCl$_3$): δ 8.41 (2H, d, J=4.5 Hz), 8.09 (2H, d, J=7.5 Hz), 7.82 (2H, d, J=4.5 Hz), 7.51-7.56 (2H, m), 7.37 (2H, d, J=8.4 Hz), 7.22-7.27 (2H, m), 4.46 (4H, t, J=7.5 Hz), 3.62-3.73 (2H, m), 1.76-1.86 (4H, m), 1.48 (6H, s), 1.46 (6H, s), 1.22-1.34 (4H, m); $^{13}$C NMR (75 MHz, CDCl$_3$) δ 150.6, 142.0, 138.5, 133.5, 129.9, 128.3, 121.7, 121.6, 119.8, 112.7, 109.8, 45.5, 31.7, 30.7, 27.2, 23.1, 23.0; ESI-MS m/z: 503.4 (M).

1,10-bis[1-isopropyl-β-carboline-9-yl) decane (40)

to give yellow oil 0.18 g, 36% yield. $^1$H NMR (300 MHz, CDCl$_3$): δ 8.42 (2H, d, J=5.1 Hz), 8.09 (2H, d, J=7.8 Hz), 7.81 (2H, 5.1 Hz), 7.53-7.58 (2H, m), 7.43 (2H, d, J=8.4 Hz), 7.22-7.27 (2H, m), 4.48 (4H, t, J=7.8 Hz), 3.68-3.81 (2H, m), 1.79-1.89 (4H, m), 1.52 (6H, s), 1.49 (6H, s), 1.28-1.42 (12H, m); $^{13}$C NMR (75 MHz, CDCl$_3$): δ 150.7, 142.0, 138.4, 133.6, 129.9, 128.2, 121.7, 121.5, 119.7, 112.7, 109.9, 45.8, 31.7, 30.6, 29.7, 29.6, 27.3, 23.1; ESI-MS m/z: 559.5 (M$^+$).

Example 14

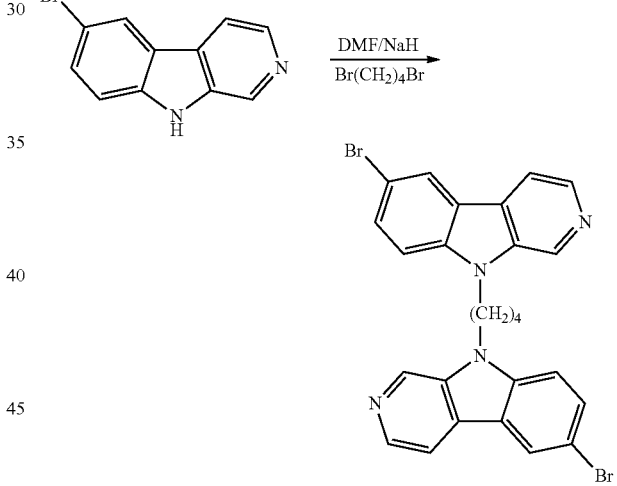

41

Synthesis of 1,4-bis[6-bromo-βcarboline-9-yl) butane (41)

A solution of 6-bromo-β-carboline ((0.25 g, 1 mmol) and 60% NaH (2.5 mmol) in DMF (20 ml) was stirred at room temperature in 100 ml round-bottomed flask. After 5 min, the 1,4-bisbromobutane (0.5 mmol) was added and the reaction mixture was stirred at 60° C. for 8-20 h, TLC detection (eluent:methanol) until the reaction completed. The reaction mixture was poured into 100 ml water and extracted with CH$_2$Cl$_2$. The extract liquor was merged extract liquor, washed with water and saturated brine, then dried with anhydrous NaSO$_4$, the solvent was removed under reduced pressure to give crude product, which was purified vis silica gel column chromatography (CH$_2$Cl$_2$/CH$_3$OH (v/v)=10:1). The eluent containing target product was collected, concentrated under reduced pressure to give the title compound (white solid). 0.14 g. 51% yield. mp 316-317° C. $^1$H NMR (300 MHz, CDCl$_3$): δ 8.78 (2H, s), 8.46 (2H, d, J=5.1 Hz), 8.20 (2H, d, J=1.8 Hz), 7.87 (2H, dd, J=5.1 Hz, 0.9 Hz), 7.55 (2H, dd, J=8.7 Hz, 1.8 Hz), 7.07 (2H, d, J=8.7 Hz), 4.28-4.32 (4H, m), 1.92-1.98 (4H, m); ESI-MS m/z: 549.1 (M$^+$).

Example 15

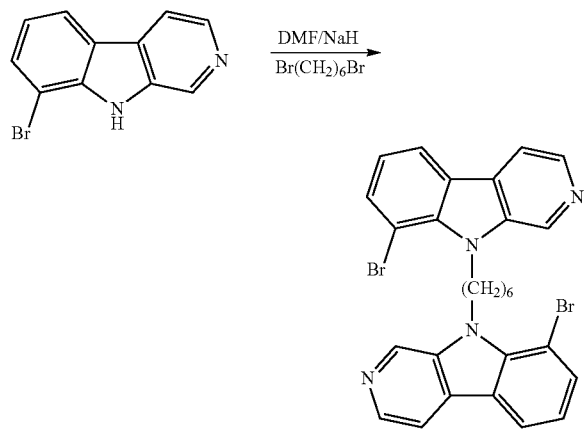

Synthesis of 1,6-bis(8-bromo-β-carboline-9-yl) hexane (42)

A solution of 8-bromo-β-carboline (2 mmol) and 60% NaH (5 mmol) in DMF (30 ml) was stirred at room temperature in 100 ml round-bottomed flask. After 5 min, the dihalogenated alkane (1 mmol) was added and the reaction mixture was stirred at 60° C. for 8-20 h, TLC detection (eluent:methanol) until the reaction completed. The reaction mixture was poured into 100 ml water and extracted with CH$_2$Cl$_2$. The extract liquor was merged extract liquor, washed with water and saturated brine, then dried with anhydrous NaSO$_4$, the solvent was removed under reduced pressure to give crude product, which was purified vis silica gel column chromatography (CH$_2$Cl$_2$/CH$_3$OH (v/v)=50:1). The eluent containing target product was collected, concentrated under reduced pressure to give the title compound.

to give white solid 0.2 g, 37% yield. $^1$H NMR (500 MHz, CDCl$_3$): δ 8.89 (2H, s), 8.49 (2H, d, J=5.5 Hz), 8.09 (2H, dd, J=1.0 Hz, 7.5 Hz), 7.91 (2H, d, J=5.5 Hz), 7.72 (2H, dd, J=1.0 Hz, 7.5 Hz), 7.11 (2H, t, J=7.5 Hz), 4.79 (4H, t, J=7.5 Hz), 1.89-1.93 (4H, m), 1.46-1.49 (4H, m); $^{13}$C NMR (100 MHz, CDCl$_3$): δ 139.5, 137.3, 133.7, 132.6, 127.8, 124.4, 120.9, 120.7, 114.2, 103.4, 44.3, 30.7, 26.5; ESI-MS m/z: 577.8 (M).

Example 16

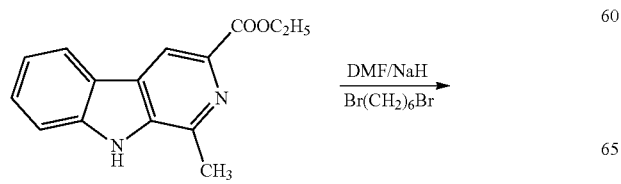

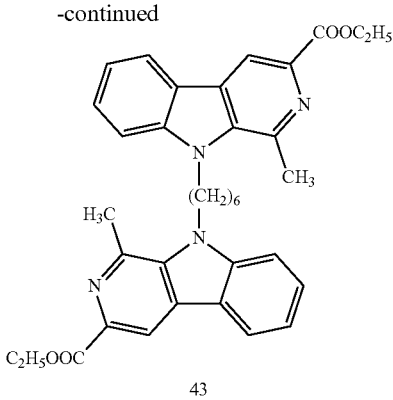

Synthesis of 1,6-bis(3-ethyoxylcarbonyl-1-methyl-β-carboline-9-yl) hexane (43)

Ethyl 1-methyl-β-carboline-3-carboxylate (2 mmol), 60% NaH (5 mmol), DMF (30 ml) and dihalogenated alkane (1 mmol) were mixed, the reaction mixture was stirred at 60° C. for 8-20 h, TLC detection (eluent:methanol) until reaction completed. The reaction mixture was poured into 100 ml water and extracted with CH$_2$Cl$_2$. The extract liquor was merged extract liquor, washed with water and saturated brine, then dried with anhydrous NaSO$_4$, the solvent was removed under reduced pressure to give crude product, which was purified vis silica gel column chromatography (CH$_2$Cl$_2$/CH$_3$OH (v/v)=50:1). The eluent containing target product was collected, concentrated under reduced pressure to give the title compound (to give white solid) 0.32 g, 54% yield. mp 268-269° C. $^1$H NMR (300 MHz, CDCl$_3$): δ 8.73 (2H, s), 8.15 (2H, d, J=7.8 Hz), 7.55-7.60 (2H, m), 7.29-7.42 (4H, m), 4.48-4.56 (8H, m), 2.99 (6H, s), 1.77-1.87 (4H, m), 1.49 (6H, t, J=7.2 Hz), 1.38-1.44 (4H, m); $^{13}$C NMR (75 MHz, CDCl$_3$): δ 166.2, 141.9, 141.4, 137.1, 136.7, 129.1, 128.7, 121.9, 121.8, 120.8, 116.5, 110.2, 61.7, 45.1, 31.2, 27.1, 24.5, 14.9; ESI-MS m/z: 590.1 (M$^+$).

Example 17

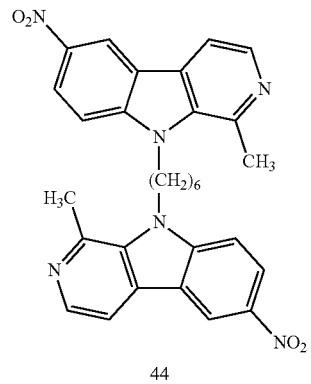

Synthesis of 1,6-bis(6-nitro-1-methyl-β-carboline-9-yl) hexane (44)

6-nitro-1-methyl-β-carboline (0.45 g, 2 mmol), 60% NaH (5 mmol), DMF (30 ml) and dihalogenated alkane (1 mmol) were mixed, the reaction mixture was stirred at 60° C. for 8-20 h, TLC detection (eluent:methanol) until the reaction completed. The reaction mixture was poured into 100 ml water and extracted with $CH_2Cl_2$. The extract liquor was merged extract liquor, washed with water and saturated brine, then dried with anhydrous $NaSO_4$, the solvent was removed under reduced pressure to give crude product, which was purified vis silica gel column chromatography ($CH_2Cl_2/CH_3OH$ (v/v)=50:1). The eluent containing target product was collected, concentrated under reduced pressure to give the title compound (ive yellow solid) 0.32 g, 60% yield. ESI-MS m/z: 536.9.

Pharmacological Experiments

Example 18

Antitumor Screening Test In Vitro

Cell lines: BGC (human gastric cancer cells), A375 (human malignant melanoma cells), 769-P (human renal carcinoma cells), KB (human oral epidermoid carcinoma cells), SK-OV-3 (human ovarian cancer cells), etc, were selected, and the test method was the MTT assay. Cisplatin was as a positive control.

Specific methods are as follows: cells growing well in the logarithmic phase were seeded in 96-well plates at a concentration of $1\times10^4$ cells/ml, and then were placed in 37° C., containing 5% $CO_2$ incubator for 24 hours. After discarding the old solution, changed fresh medium, and added sterilization treatment compound, and then cultured for 48 hours. After discarding the culture medium, 20 ul RPMI1640 medium containing 5 mg/ml MTT were added to each well in 96-well plates and cells were cultured for 4 hours. After the supernatant was carefully removed, 100 μl DMSO was added to each well, and the plates were Oscillated about 10 min to dissolve the precipitate, followed by detecting OD value in wavelength 490 nm by the microplate reader. Cell survival rate for each sample concentrations was determined by the following formula:

The mean survival rate %=the average OD value of sample group/the average OD value of control group×100%

Morphological studies by mapping with the logarithm of the drug concentration and the mean survival rate % of each sample to obtain $IC_{50}$ values for each sample.

The test results are shown in Table 1.

TABLE 1

The chemical structure and anti-tumor activity of bis-β- carboline alkali derivative

| NO. | $IC_{50}$ (uM) | | | | |
| --- | --- | --- | --- | --- | --- |
| | BGC | A375 | 769-P | KB | SK-OV-3 |
| 1 | 59.7 | >300 | 199 | >300 | >300 |
| 2 | 23.5 | 10.2 | 15.3 | >300 | >300 |
| 3 | 13.8 | 10.8 | 12.8 | 13.9 | 38.9 |
| 4 | >300 | 286 | 53.0 | >300 | 212 |
| 5 | >300 | 285 | >300 | >300 | 33.5 |
| 6 | 251.8 | 69.5 | 144.9 | 160.4 | 26.4 |

TABLE 1-continued

The chemical structure and anti-tumor activity of bis-β- carboline alkali derivative

| NO. | $IC_{50}$ (uM) | | | | |
| --- | --- | --- | --- | --- | --- |
| | BGC | A375 | 769-P | KB | SK-OV-3 |
| 7 | 22.3 | 13.1 | 6.5 | 6.4 | 4.8 |
| 8 | >300 | >300 | >300 | >300 | 18.8 |
| 9 | >300 | >300 | 51.7 | >300 | 96.8 |
| 10 | 133.6 | 38.0 | 149.2 | 87.9 | 16.9 |
| 11 | >300 | >300 | 3.1 | >300 | >300 |
| 12 | >300 | 67.2 | 290.8 | >300 | 61.9 |
| 13 | >300 | >300 | 16.2 | >300 | 8.5 |
| 14 | 75.7 | 6.2 | 65.6 | 2.8 | 7.1 |
| 15 | 58.6 | <1.38 | 81.0 | 5.0 | 1.7 |
| 17 | >300 | 35.3 | >300 | 155.4 | 11.7 |
| 18 | 103.8 | 112.8 | 113.9 | 38.6 | 10.2 |
| 19 | >300 | 5.9 | 16.8 | >300 | >300 |
| 20 | >300 | 4.0 | 3.3 | 7.6 | >300 |
| 21 | >300 | >300 | 4.3 | >300 | >300 |
| 22 | >300 | >300 | >300 | >300 | 63.4 |
| 23 | 8.5 | 3.8 | >300 | 6.8 | 5.5 |
| 24 | >300 | >300 | 56.0 | >300 | >300 |
| 25 | 193.5 | 18.5 | 95.4 | 19.8 | 17.1 |
| 26 | >300 | 43.3 | 40.0 | 111.6 | 100.6 |
| 28 | >300 | 217.5 | 44.6 | >300 | >300 |
| 29 | 24.1 | 13.0 | 132.2 | 15.7 | >300 |
| 30 | >300 | >300 | >300 | >300 | 68.3 |
| 31 | 269.7 | 85.3 | >300 | >300 | 36.8 |
| 32 | 14.1 | 5.3 | >300 | 13.3 | 14.9 |
| 33 | >300 | >300 | >300 | >300 | 67.6 |
| 34 | >300 | 32.1 | >300 | >300 | >300 |
| 35 | >300 | 23.2 | >300 | >300 | >300 |
| 36 | >300 | 10.4 | 82.1 | >300 | >300 |
| 37 | >300 | 7.0 | 3.8 | >300 | >300 |
| 38 | >300 | >300 | 1.8 | >300 | >300 |
| 39 | >300 | 53.5 | 18.5 | 253 | 31.8 |
| 40 | >300 | 19.6 | 4.6 | >300 | >300 |
| 41 | >300 | >300 | 3.1 | >300 | 8.9 |
| Cisplatin | 17.3 | 39.2 | 11.6 | 13.1 | 4.2 |

Example 19 Acute Toxicity Test in Mice Embodiment

Kunming mice (provided by Shanghai Experimental Animal Center, Chinese Academy of Sciences, Certificate of Conformity: shanghai No. 107), weight 19-20 g, male: female=1:1, 10 mice per group. Solvent: 0.9% saline and 0.5% CMC-Na solution. According to pre-test results, design 5 dose gradient for each sample, dose spacing was 0.8 times. After weighing each sample, plus a small amount of Tween 80 to increase solubility, and then gradually add 0.5% CMC-Na solution to the desired concentration. Experimental volume is 0.5 ml/20 g mouse. A single intraperitoneal administration is used. Kunming mice were taken and grouped randomly by gender, and intraperitoneal administration according to dose designation was set to observe the immediate reaction after administration in mice. Dead animals were dissected to observe, surviving animals continued to observe two weeks, and the animal deaths in two weeks were recorded. After two weeks, surviving animals were dissected, observed substantial organ lesions, and the organs having substantive lesions were further for histological examination. According to the number of deaths in each group of animals, calculating the median lethal dose ($LD_{50}$ value) by Bliss method, and further, calculating the maximum tolerated dose (MTD) for less toxic compounds.

The test results are shown in Table 2 below.

Example 20 Anti-Tumor Test In Vivo

Kunming mice (provided by Shanghai Experimental Animal Center, Chinese Academy of Sciences, Certificate of Conformity: shanghai No. 107), weight 18-20 g, male or female can be, the same sex were used in each batch of experimental. Anti-tumor experiments C57BL/6 mice and Kunming mice were 8-10 mice each group, and two negative control groups; the source of tumor was Lewis lung carcinoma, CT-26 colon cancer, 5180 sarcoma (provided by Pharmacology of the Shanghai Pharmaceutical Industry Institute and maintained); solvent was 0.9% saline and 0.5% CMC-Na solution; test drug set high and low dose groups, respectively, ⅕ and ⅒ of LD50 value by intraperitoneal administration of a single dose of the drug as a benchmark. Weigh each test sample, plus a small amount of Tween-80 to increase solubility, and gradually add 0.5% CMC-Na solution to the desired concentration. Experimental volume is 0.5 ml/20 g mouse. Intraperitoneal administration, once a day for consecutive 10 days, a total of 10 times administration. An equal volume of appropriate solvent was given as negative control, the same is intraperitoneal administration once a day for 10 days. Cyclophosphamide (CTX) was administrated by Intraperitoneal by 30 mg/kg dose, once a day for seven days as positive control. The in vivo anti-tumor model is made by subcutaneously inoculating tumor source: take tumor source in vigorous growth under sterile conditions, prepare cell suspension to about $1\times10^7$/ml by homogenizing method, inoculate subcutaneously by 0.2 ml/the respective host mouse, and the next day administer examples and positive or negative controls according to experimental design scheme, about three weeks the animals in each group were sacrificed, dissected tumor was weighed. The inhibitory rate was calculated as follows:

Inhibition rate %=[(mean tumor weight of negative control group−mean tumor weight of treatment group)/the mean tumor weight of negative control group]×100%

After the administration, observe the immediate response of mice, especially observe whether the focus jump, tremor, twisting and other neurological toxicity is appeared.

The test results were shown in Table 2 below.

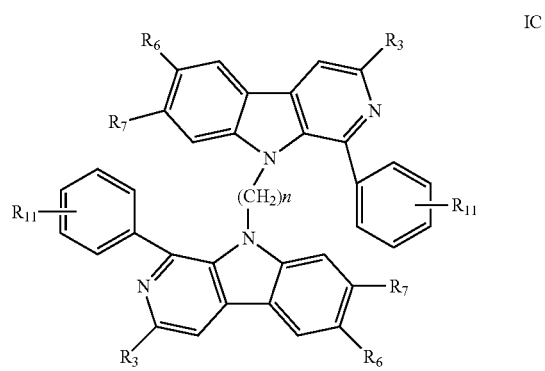

$R_3$ is a substituent selected from the group consisting of hydrogen, C1-6 alkoxy-CO—, and C1-4alkyl-NH—CO—;

$R_6$ is a substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched mono- and bis-alkylamino group, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, and cyano;

$R_7$ is a substituent selected from the group consisting of hydrogen, substituted or unsubstituted C1-4 linear or branched alkyl, hydroxyl, substituted or unsubstituted

TABLE 2

Acute toxicity and anti-tumor acitivity test results of bis-β-carboline compounds in mice

| Compound NO. | acute toxicity $LD_{50}$ | neurotoxicity | dose (mg) | inhibition rate (%) | | |
|---|---|---|---|---|---|---|
| | | | | CT-26 colorectal cancer | Lewis lung cancer | sarcoma S180 |
| Harmine | 59.0 | +++ | 10 | — | 34.1 | 15.3 |
| 1 | 200 | − | 40 | 39.7 | 34.2 | — |
| 2 | 150 | − | 30 | 48.6 | 42.5 | 43.8 |
| 7 | 200 | − | 20 | 50.8 | 40.4 | 56.2 |
| 9 | 200 | − | 40 | 39.6 | 42.1 | — |
| 11 | 200 | − | 40 | 43.5 | 34.9 | — |
| 14 | 50 | − | 10 | 45.5 | 38.1 | — |
| 17 | 200 | − | 40 | 40.2 | 39.5 | 41.6 |
| 19 | 200 | − | 40 | 45.8 | 43.3 | — |
| 22 | 200 | − | 40 | 42.1 | 36.8 | — |
| 25 | 220 | − | 40 | 51.2 | 49.6 | 40.6 |
| 26 | 200 | − | 40 | 45.2 | 42.8 | 40.8 |
| 27 | 300 | − | 60 | 47.8 | 42.6 | 38.6 |
| 32 | 250 | − | 50 | 50.6 | 43.2 | 40.5 |
| 34 | 250 | − | 50 | 43.1 | 39.5 | 45.8 |
| CTX | | | 50 | 97.2 | 97.8 | 85.6 |

The invention claimed is:

1. A compound, or a physiologically acceptable salt thereof wherein, the compound is represented by the general formula IC:

C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched mono- and bis-alkylamino group, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, and cyano;

$R_{11}$ represents one or more substituents, can connect with phenyl at any location which can be connected, and is selected from the group consisting of hydrogen, hydroxyl, mercapto, amino, aldehyde, carboxyl, carbamoyl, halogen, nitro, cyano, C1-4 alkyl, C1-4 alkoxy, C1-4 alkylamino group, and C1-4 alkoxy C1-4 alkyl group; and, substituents on the substituted or unsubstituted C1-4 linear or branched alkyl are selected from the group consisting of hydroxy, mercapto, amino, aldehyde, carboxyl, carbamoyl, fluoro, chloro, bromo, nitro, and cyano, and n is selected from the group consisting of natural numbers from 2-12.

2. A compound, or a physiologically acceptable salt thereof, wherein the compound is represented by the general formula ID:

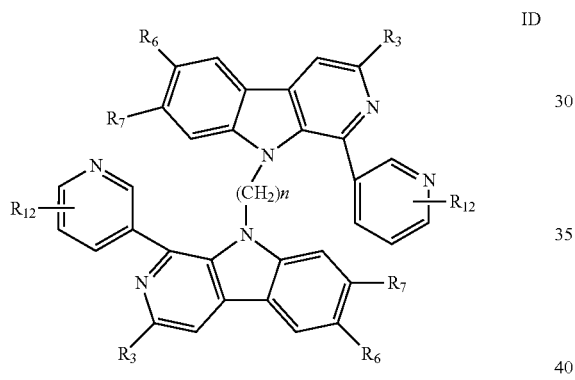

ID $R_3$ is a substituent selected from the group consisting of hydrogen, C1-6 alkoxy-CO—, and C1-4alkyl-NH—CO—;

$R_6$ is a substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched mono- and bis-alkylamino group, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, and cyano;

$R_7$ is a substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched mono- and bis-alkylamino group, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, and cyano;

$R_{12}$ represents one or more substituents, can connect with pyridine at any location which can be connected, and is selected from the group consisting of hydrogen, hydroxyl, mercapto, amino, aldehyde, carboxyl, carbamoyl, halogen, nitro, cyano, C1-4 alkyl, C1-4 alkoxy, C1-4 alkylamino group, and C1-4 alkoxy C1-4 alkyl group substituents on the substituted or unsubstituted C1-4 linear or branched alkyl are selected from the group consisting of hydroxy, mercapto, amino, aldehyde, carboxyl, carbamoyl, fluoro, chloro, bromo, nitro, and cyano; n is selected from the group consisting of the natural numbers from 2 to 12.

3. A compound or a physiologically acceptable salt thereof, wherein the compound is represented by the general formula IE:

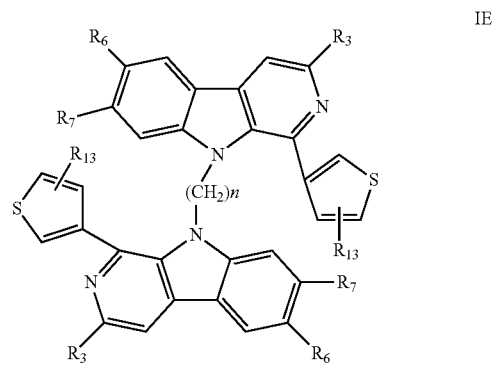

IE $R_3$ is a substituent selected from the group consisting of hydrogen, C1-6 alkoxy-CO—, and C1-4alkyl-NH—CO—;

$R_6$ is a substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched mono- and bis-alkylamino group, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, and cyano;

$R_7$ is a substituent selected from the group consisting of hydrogen, substituted or unsubstituted C1-4 linear or branched alkyl, hydroxyl, substituted or unsubstituted C1-4 linear or branched alkoxy, sulfonate group, substituted or unsubstituted C1-4 linear or branched alkylthio, C1-4 alkoxy C1-4 alkyl group, amino group, substituted or unsubstituted C1-4 linear or branched mono- and bis-alkylamino group, aldehyde, substituted or unsubstituted C1-4 linear or branched alkyl acyl, substituted or unsubstituted C1-4 linear or branched alkyloxy acyl, carboxyl, substituted or unsubstituted C1-4 linear or branched alkyl acyloxy, carbamoyl, substituted or unsubstituted C1-4 linear or branched alkyl acylamino group, substituted or unsubstituted C1-4 linear or branched alkyl acylamino group, halogen, nitro, and cyano;

$R_{13}$ represents one or more substituents, can connect with thiophere at any location which can be connected, and is selected from the group consisting of hydrogen, hydroxyl, mercapto, amino, aldehyde, carboxyl, carbamoyl, halogen, nitro, cyano, C1-4 alkyl, C1-4 alkoxy, C1-4 alkylamino group, and C1-4 alkoxy C1-4 alkyl group;

substituents on the substituted or unsubstituted C1-4 linear or branched alkyl are selected from the group consisting of hydroxy, mercapto, amino, aldehyde, carboxyl, carbamoyl, fluoro, chloro, bromo, nitro, and cyano; and, n is selected from the group consisting of the natural numbers from 2 to 12.

\* \* \* \* \*